(12) United States Patent
Nakamura et al.

(10) Patent No.: US 10,996,174 B2
(45) Date of Patent: May 4, 2021

(54) GAS SENSING ELEMENT

(71) Applicant: Nitto Denko Corporation, Osaka (JP)

(72) Inventors: Koichi Nakamura, Rockledge, FL (US); Nahid Mohajeri, Rockledge, FL (US); Yu-chu Chen, Evanston, IL (US); Kujtim Bizati, Lakewood, NJ (US); Shinji Inokuchi, Tinton Falls, NJ (US); Namiko Suzuki, Osaka (JP); Hiroyuki Higuchi, Osaka (JP); Masahiko Hirose, Osaka (JP); Masaya Nishigawara, Osaka (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 16/070,068

(22) PCT Filed: Feb. 17, 2018

(86) PCT No.: PCT/US2018/018531
§ 371 (c)(1),
(2) Date: Jul. 13, 2018

(87) PCT Pub. No.: WO2018/152430
PCT Pub. Date: Aug. 23, 2018

(65) Prior Publication Data
US 2020/0003697 A1    Jan. 2, 2020

Related U.S. Application Data

(60) Provisional application No. 62/460,490, filed on Feb. 17, 2017, provisional application No. 62/483,521, filed on Apr. 10, 2017.

(51) Int. Cl.
*G01N 21/78* (2006.01)
*G01M 3/22* (2006.01)
(Continued)

(52) U.S. Cl.
CPC ............ *G01N 21/783* (2013.01); *G01M 3/04* (2013.01); *G01M 3/22* (2013.01); *G01N 31/223* (2013.01);
(Continued)

(58) Field of Classification Search
CPC ............ G01N 21/783; G01N 33/0027; G01N 31/223; G01N 33/0062; G01N 33/005; G01N 33/0009; G01M 3/22; G01M 3/04
See application file for complete search history.

(56) References Cited

U.S. PATENT DOCUMENTS

| | | |
|---|---|---|
| 4,309,520 A | 1/1982 | Blizzard |
| 4,420,567 A | 12/1983 | McMahon et al. |

(Continued)

FOREIGN PATENT DOCUMENTS

| | | |
|---|---|---|
| JP | H08-253742 | 10/1996 |
| JP | 2005-345338 | 12/2005 |

(Continued)

OTHER PUBLICATIONS

Hartmann, "Passive Leak Detection Using Commercial Hydrogen Colorimetric Indicator" NREL Technical Report Sep. 2016, pp. 1-27 (Year: 2016).*

(Continued)

*Primary Examiner* — Dennis White
(74) *Attorney, Agent, or Firm* — IPUSA, PLLC

(57) ABSTRACT

A gas sensing element includes a gas detection layer including a pigment, the gas detection layer including a first surface; and a backing material disposed on the first surface of the gas detection layer. When reducing gas causes the gas sensing element to change in color, a color change $\Delta L^*$ of the gas sensing element is greater than or equal to 5.

19 Claims, 19 Drawing Sheets

ILLUSTRATION PURPOSES ONLY,
NOT TO SCALE

(51) Int. Cl.
  *G01N 31/22* (2006.01)
  *G01N 33/00* (2006.01)
  *G01M 3/04* (2006.01)

(52) U.S. Cl.
  CPC ....... *G01N 33/005* (2013.01); *G01N 33/0027* (2013.01); *G01N 33/0062* (2013.01)

(56) References Cited

U.S. PATENT DOCUMENTS

| | | | |
|---|---|---|---|
| 5,248,739 | A | 9/1993 | Schmidt et al. |
| 5,430,293 | A | 7/1995 | Sato et al. |
| 5,508,509 | A * | 4/1996 | Yafuso ................ G01N 31/223 250/216 |
| 5,529,841 | A | 6/1996 | Neihof |
| 5,849,073 | A * | 12/1998 | Sakamoto ............. B82Y 30/00 106/437 |
| 7,851,758 | B1 | 12/2010 | Scanlon et al. |
| 8,652,993 | B2 | 2/2014 | Mohajeri |
| 2002/0083883 | A1 | 7/2002 | Inoue et al. |
| 2003/0186013 | A1 | 10/2003 | Dhaler |
| 2007/0224081 | A1 | 9/2007 | Bokerman et al. |
| 2007/0251822 | A1 | 11/2007 | Hoagland et al. |
| 2008/0213527 | A1 | 9/2008 | Nonaka et al. |
| 2008/0259341 | A1 | 10/2008 | Short et al. |
| 2010/0253376 | A1 | 10/2010 | Grosse Bley et al. |
| 2011/0300296 | A1 * | 12/2011 | Sherman ............... C08F 220/06 427/208.4 |
| 2012/0040180 | A1 | 2/2012 | Husemann et al. |
| 2013/0005045 | A1 | 1/2013 | Captain et al. |
| 2014/0028459 | A1 | 1/2014 | Solomon |
| 2014/0032160 | A1 | 1/2014 | Rella et al. |
| 2014/0051567 | A1 | 2/2014 | Mohajeri |
| 2014/0170535 | A1 | 6/2014 | Yano et al. |
| 2014/0379299 | A1 | 12/2014 | Kulkarni et al. |
| 2015/0260656 | A1 | 9/2015 | Zilberstein et al. |
| 2016/0327533 | A1 | 11/2016 | Jin et al. |

FOREIGN PATENT DOCUMENTS

| | | |
|---|---|---|
| JP | 2006-084399 | 3/2006 |
| JP | 2016-176778 | 10/2016 |

OTHER PUBLICATIONS

Gas Leak Detector is Simple and Inexpensive, Nasa Tech Brief, Dec. 1966, p. 1. (Year: 1966).*
International Search Report for PCT/US18/18486 dated Apr. 25, 2018.
International Search Report for PCT/US18/18531 dated Apr. 20, 2018.
International Search Report for PCT/US18/18532 dated Apr. 20, 2018.
Office Action dated Mar. 4, 2020 issued with respect to the related U.S. Appl. No. 16/070,610.
Office Action dated Mar. 30, 2020 issued with respect to the related U.S. Appl. No. 16/070,069.
Office Action dated Jun. 30, 2020 issued with respect to the related U.S. Appl. No. 16/070,610.
Office Action dated Jul. 30, 2020 issued with respect to the related U.S. Appl. No. 16/070,069.
Extended European search report dated Dec. 9, 2020 issued with respect to the corresponding European patent application No. 18755089.2.
Kazemi Alex A et al: "Plastic Optical Fiber Hydrogen Detection Sensor Systems for Harsh Environment in Aerospace Application", Photonic Applications for Aerospace, Transportation, and Harsh Environment III, Proc. of SPIE, vol. 8368, No. 1, May 11, 2012, pp. 1-15, XP060004035.
Extended European search report dated Dec. 16, 2020 issued with respect to the related European patent application No. 18754268.3.
Partial supplementary European search report dated Dec. 2, 2020 issued with respect to the related European patent application No. 18753874.9.
Office Action dated Mar. 3, 2021 issued with respect to the related U.S. Appl. No. 16/070,069.
Extended European Search Report dated Mar. 12, 2021 issued with respect to the related European Patent Application No. 18753874.9.
Kevin Hartmann et al.: "Passive Leak Detection Using Commercial Colorimetric Indicator", National Renewavle Energy Lab (NREL), Golden (CO), US, Sep. 1, 2016 (Sep. 1, 2016), pp. 1-27, XP055750573, DOI:10.2172/1326889, Retrieved from the Internet: URL:https://www.nrel.gov/docs/fy16osti/66570.pdf, [retrieved on Nov. 13, 2020] * p. 1, paragraph 2 *, *p. 2; figure 1 *, *pp. 23-24 *, *p. 27 *.

* cited by examiner

ILLUSTRATION PURPOSES ONLY,
NOT TO SCALE

FIG.7

| IMAGING DEVICE NAME | ATTRIBUTE INFORMATION | VIDEO DATA |
|---|---|---|
| FIRST IMAGING DEVICE | ·INSTALLATION POSITION: LATITUDE 1, LONGITUDE 1<br>·RESOLUTION: RESOLUTION 1 [PIXEL]<br>·FRAME RATE: fr1 [FRAME/sec] | 2015.1 ... 2016.1 ... 2017.1 |
| SECOND IMAGING DEVICE | ·INSTALLATION POSITION: LATITUDE 2, LONGITUDE 2<br>·RESOLUTION: RESOLUTION 1 [PIXEL]<br>·FRAME RATE: fr1 [FRAME/sec] | |
| ... | ... | |
| n TH IMAGING DEVICE | ·INSTALLATION POSITION: LATITUDE n, LONGITUDE n<br>·RESOLUTION: RESOLUTION 1 [PIXEL]<br>·FRAME RATE: fr1 [FRAME/sec] | |

FIG.8

| IDENTIFICATION NUMBER | ELEMENT INFORMATION | | | | | |
|---|---|---|---|---|---|---|
| | GAS DETECTION ELEMENT TYPE | ATTACHMENT LOCATION | ATTACHMENT COMPONENT | ATTACHMENT TIME | ATTACHMENT WORKER |
| G001 | TYPE A | PIPE I | FLANGE I | 2015.2.4 | ... |
| G002 | TYPE B | PIPE II | FLANGE I | 2016.6.8 | ... |
| ... | ... | ... | ... | ... | ... |
| G00n | TYPE A | PIPE V | FLANGE II | 2016.9.18 | ... |

1400

GAS SENSING ELEMENT

The present application claims priority to U.S. Provisional Patent Application No. 62/460,490, filed on Feb. 17, 2017, U.S. Provisional Patent Application No. 62/483,521, filed on Apr. 10, 2017, and International Application PCT/US18/18486 filed on Feb. 16, 2018, the contents of which are incorporated herein by reference in their entirety.

TECHNICAL FIELD

The disclosed embodiments relate to a gas sensing element (also referred to herein as "gas detection element").

BACKGROUND ART

Technology has been developed for gas detection tape as described in U.S. Pat. Nos. 8,591,818; 8,652,993; and 8,703,642 for high temperature environments.

The conventional hydrogen gas detection sheet includes forming a hydrogen gas detection layer on a backing material, as described in, for example, U.S. Pat. No. 8,591,818. However, a hydrogen gas detection sheet having such a configuration does not have substantial adhesion to its measurement targets (i.e., junctions, flanges, valves, etc. to be detected for gas leakage).

Therefore, when actually using the conventional hydrogen gas detection sheet, an auxiliary tape and an adhesive, etc., are used to fix the hydrogen gas detection sheet to the measurement target. That is, the hydrogen gas detection sheet is fixed to the measurement target, for example, by attaching the adhesive tape as an auxiliary tape across the hydrogen gas detection sheet and the measurement target, in a state in which one side of the hydrogen gas detection layer of the hydrogen gas detection sheet is in contact with the setting side of the measurement target.

However, the above method may be a factor that causes a decrease in the workability at the site. Furthermore, by the above method, a gap may be formed between the measurement target and the hydrogen gas detection layer, and this may be a factor that hampers accurate measurements.

Therefore, in order to address the above problem, one approach may be to form the hydrogen gas detection sheet by setting the hydrogen gas detection layer and an adhesive layer on the backing material during manufacturing.

However, a problem with the above configuration is that the structure of the hydrogen gas detection sheet may be complicated by setting the adhesive layer. Particularly, the adhesive layer is not involved in the hydrogen gas detection, and is essentially an unnecessary member. Rather, if an adhesive layer is present on the hydrogen gas detection layer, this adhesive layer may hamper the movement of hydrogen gas to the hydrogen gas detection layer, and the hydrogen gas may not be accurately detected.

Furthermore, in a conventional gas detection element, for example, in a situation where the concentration of the measurement target gas is low, there are cases where the color change, which occurs when contact is made with the measurement target gas, is insufficient.

In this case, in particular, when the measurement target is located away from the examining staff, it is difficult for the examining staff to determine whether there is any color change in the gas detection element.

Furthermore, for example, at a plant, etc., where hydrogen gas is used, there are cases where the piping, through which the hydrogen gas flows, is arranged at a location that is difficult to visually confirm. In these cases, in order to detect whether gas leakage has occurred, it would take significant amounts of labor and cost.

Thus, there remains a need for an improved gas detection tape composition embodiment that reduces the problems described above.

SUMMARY OF INVENTION

As a result of the need for new materials and processes, a new gas detection tape comprising chemochromic materials and a method for manufacturing the aforementioned tape can be realized to facilitate passive and efficient gas level detection.

In some embodiments, a pressure sensitive adhesive ("PSA") gas detection element is described, where the element can comprise chemochromic composition including a palladium oxide, palladium hydroxide, or palladium salts, dispersed within a polymer matrix of a siloxane crosslinked by free radical transfer reaction.

In some elements, the siloxane can comprise polydimethylsiloxane and polydimethyldiphenylsiloxanes with different percentages of phenyl content. Some initiators can be a peroxide, such as benzoyl peroxide or 2,4-dichlorobenzoyl peroxide.

In some elements, the element can further comprise a backing to form a tape. In some embodiments, the backing can comprise a polymer such as polyimide, fluorinated ethylene propylene, polyethylene, polytetrafluoroethylene, or polyethylene terephthalate. In some embodiments, the backing can be resistant to ultraviolet (UV) radiation.

In some embodiments, methods of producing a pressure sensitive gas detection adhesive are described. In some embodiments, the method can comprise: (1) contacting a treatment liquid and a chemochromic composition, the treatment liquid comprising a siloxane precursor and a peroxide initiator; and (2) heating the treatment liquid to a temperature sufficient to activate the initiator so that the precursor is crosslinked to create a polymer matrix containing the chemochromic composition. In some embodiments, the initiator can comprise a peroxide, such as benzoyl peroxide or 2,4-dichlorobenzoyl peroxide. In some embodiments, the siloxane precursor can comprise polydimethylsiloxane and polydimethyldiphenylsiloxanes with different percentages of phenyl content. In some embodiments, the chemochromic composition can comprise one or more palladium-oxide-based chemochromic elements.

For some methods, the heating step can be done at a temperature with a profile within the range of 120° C. to 200° C. for 1 to 3 minutes. In some embodiments, the heating step can further comprise an additional step of removing any solvent from the treatment liquid before the primary heating step by heating at a temperature within the range of 25° C. to 100° C. For example, in the case of 25° C., the heating time is preferably approximately 10 minutes, and in the case of 100° C., the heating time is preferably approximately 30 seconds.

Some methods can further comprise the step of applying the contacted treatment liquid and chemochromic composition in a layer on a backing, whereby the result is a tape. In some embodiments, the backing can comprise a polymer such as polyimide, polypropylene, fluorinated ethylene propylene, ethylene tetrafluoroethylene, polyethylene, polytetrafluoroethylene, perfluooroalkoxy alkanes, or polyethylene terephthalate. In some embodiments, the backing can be resistant to ultraviolet radiation.

Some methods additionally comprise the step of exposing the polymer matrix to an oxygen-containing atmosphere. In some embodiments, the step of exposing to an oxygen-containing atmosphere may comprise exposing to air. For some embodiments, the step of exposing the polymer matrix to an oxygen-containing atmosphere can comprise using an oxygen permeable release liner. In some embodiments, the step of exposing the pressure sensitive adhesive to an oxygen-containing atmosphere can comprise maintaining the physical parameters of the adhesive material to less than amount sufficient to allow contact of the resulting adhesive to the surrounding air.

In some embodiments, a gas sensing element is described. The gas sensing element includes a gas detection layer including a pigment, wherein the gas detection layer has an adhesion of greater than or equal to 0.2 N/25 mm.

In some embodiments, a gas detection layer is described. The gas detection layer includes a pigment, wherein the gas detection layer has an adhesion of greater than or equal to 0.2 N/25 mm.

A gas sensing element includes a gas detection layer including a pigment, the gas detection layer including a first surface; and a backing material disposed on the first surface of the gas detection layer. When reducing gas causes the gas sensing element to change in color, a color change $\Delta L^*$ of the gas sensing element is greater than or equal to 5.

In some embodiments, the gas detection layer has a thickness of 10 μm to 100 μm, and in a state in which the gas sensing element is wound around a pipe with a hole penetrating through the pipe from the inside of the pipe to the outside of the pipe, in a manner so as to occlude the hole, the hole having a diameter of 2 mm on a side surface of the pipe, the pipe having an inner diameter of 10 mm and having both ends open, at room temperature (25° C.), when the reducing gas is made to flow through from one end to another end of the pipe for five minutes at a flow rate of 6 ml/min, a color change $\Delta L^*$ of the gas sensing element becomes greater than or equal to 5, at a position of the hole.

In some embodiments, a gas detection system is described. The gas detection system includes (1) an output device configured to output data acquired by monitoring a gas sensing element including a gas detection layer including a pigment; and (2) an information processing apparatus configured to process the data output by the output device, wherein the information processing apparatus includes a determining unit configured to determine whether the gas sensing element has detected gas, based on the data, and a display control unit configured to display, on an indication element, information indicating the position of the gas sensing element that has detected the gas or information indicating a status of gas leakage determined based on the data, when the determining unit determines that the gas sensing element has detected the gas.

In some embodiments, gas detection system is described. The gas detection system includes (1) a gas sensing element including a gas detection layer including a pigment; (2) a gas monitoring output device in visual communication with the gas sensing element where the output device converts visual indications from the gas sensing elements into electrical data; (3) a gas detection information processing apparatus, in electrical communication with the gas monitoring output device, where the processing apparatus receives and processes the data, the information processing apparatus includes (a) a determining unit, where the unit is configured to determine whether the gas sensing element has detected gas based levels of data to a pre-stored comparison, and (b) a display control unit, the unit in electrical communication with an indication element, where the control unit provides electrical data indicating the position of the gas sensing element that has detected gas when the determining unit determines upon said sensing element detecting gas; (4) an indication element, whereby information indicating the position of the gas sensing element that has detected gas or information indicating a status of gas leakage determined based on the data is displayed when gas is detected by said sensing element.

In some embodiments, gas detection method is described. The gas detection method includes outputting data acquired by monitoring a gas sensing element including a gas detection layer including a pigment; determining whether the gas sensing element has detected gas, based on the data; and communicating with an indication element in order to provide information indicating a position of the gas sensing element that has detected the gas or information indicating a status of gas leakage determined based on the data, when the gas sensing element is determined to have detected the gas.

These and other embodiments are described in greater detail below.

BRIEF DESCRIPTION OF DRAWINGS

FIG. 7 is a depiction of an example of video data stored in a video data storage unit.

FIG. 8 is a depiction of an example of element information stored in an element information storage unit.

DESCRIPTION OF EMBODIMENTS

Figure 1:
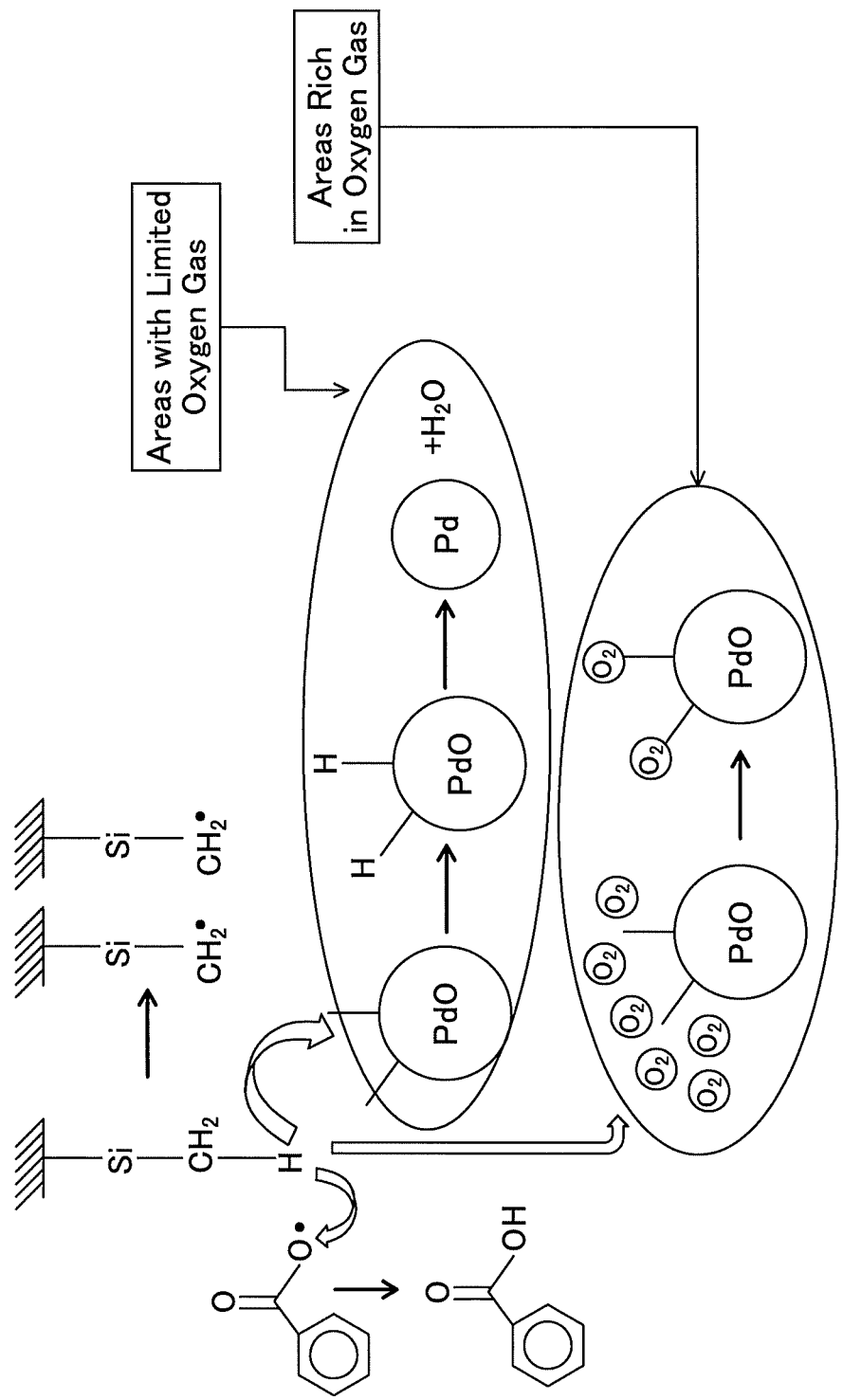
FIG. 1 is a depiction of one possible mechanism for a premature pigment color change as a result of crosslinking.
Figure 2:
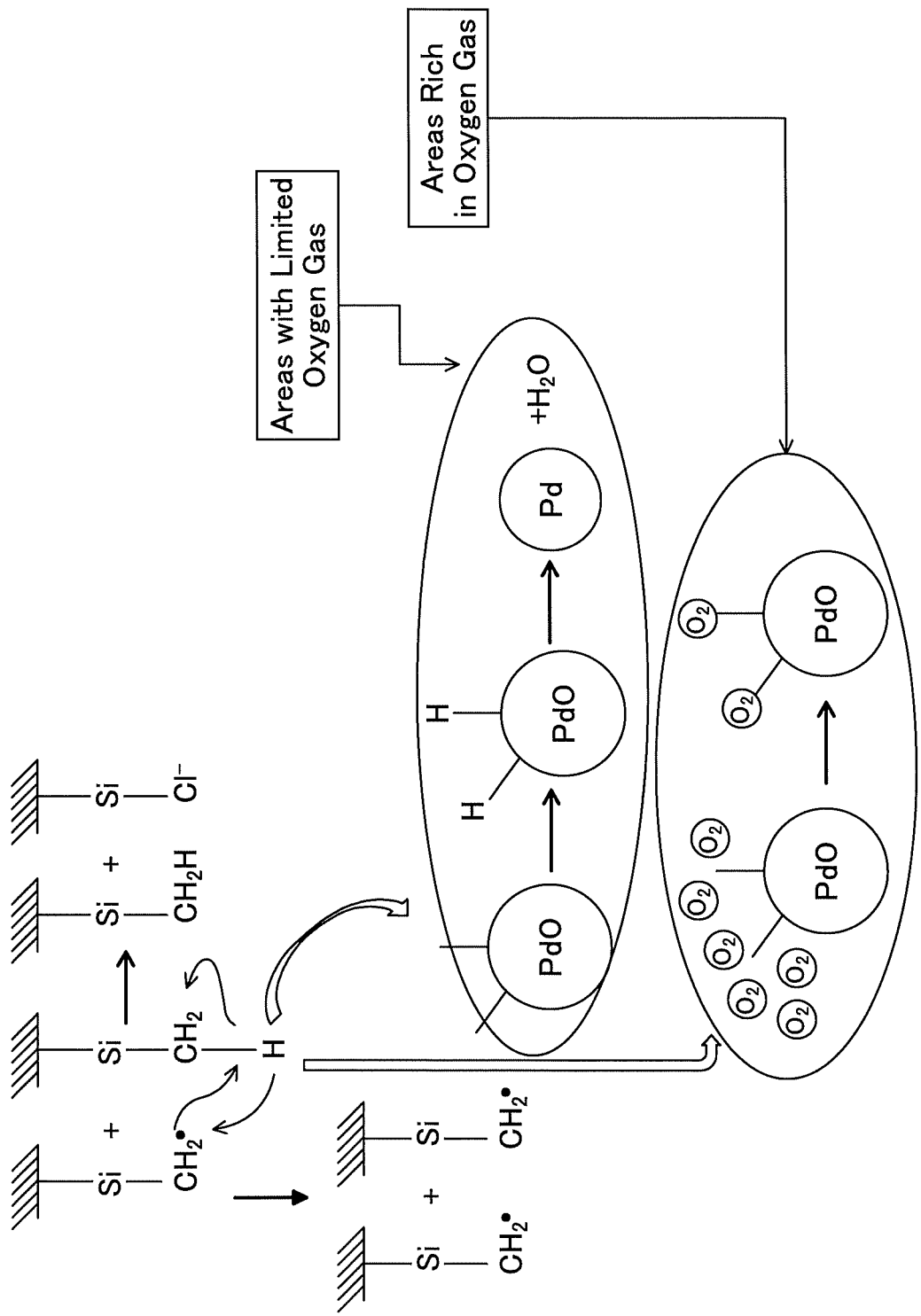
FIG. 2 is a depiction of another possible mechanism for premature pigment color change as a result of crosslinking.

It was confirmed that the presence of oxygen, which is present in the atmosphere or that which is artificially applied, which can penetrate the pressure sensitive adhesive layer, can cover the surface of the chemochromic reagent, thereby preventing the adsorption of low concentration/residual hydrogen and/or hydrogen molecules onto the detection compound. For example, if the detection compound formula is PdO, then oxygen present in the tape or in the atmosphere would prevent the reduction of PdO to Pd. While not wanting to be limited by theory, it is thought that the presence of oxygen would prevent adsorption of hydrogen on the PdO surface by either elimination of the radicals and/or blocking the active sites. It is thought that there are at least two possible mechanisms for the color change; each is detailed in FIG. 1 and FIG. 2. Increasing the presence of oxygen in the gas detection elements can be done by formulating specific embodiments of elements and/or by following specific methods for fabricating the aforementioned elements.

I. Pressure Sensitive Adhesive Gas Detection Element

Figure 3:
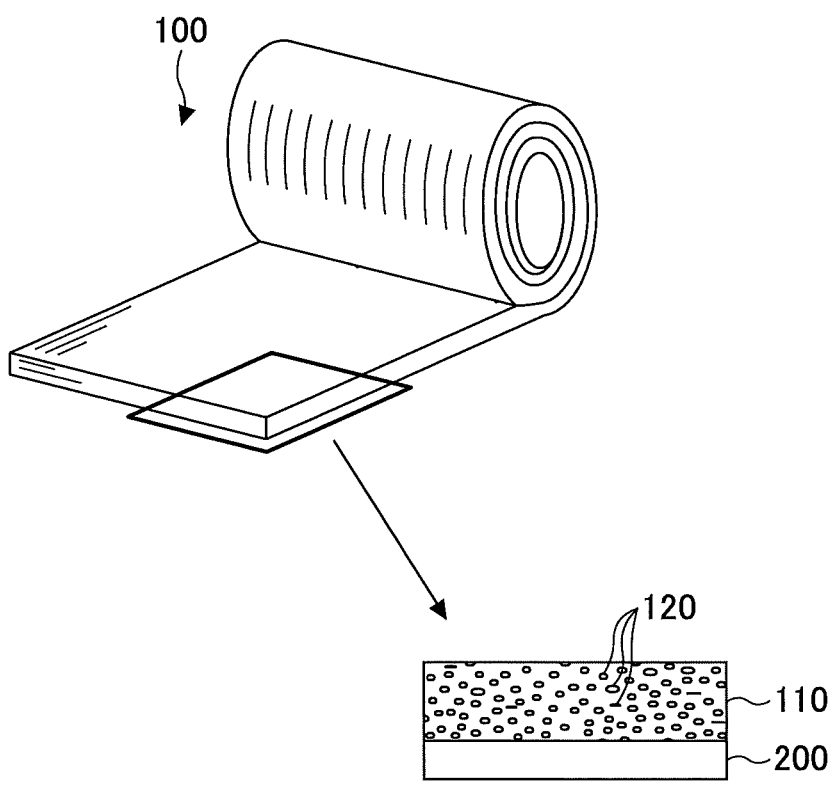
FIG. 3 is an illustration of a possible embodiment of a gas detection element.

In one embodiment, a gas detection element is described. In some embodiments, the gas detection element can detect the presence of reducing gases. In some embodiments, reducing gases detected can include hydrogen gas. In some embodiments, the gas detection element can comprise a pressure sensitive adhesive, or a pressure sensitive adhesive gas detection element. In some embodiments, as shown in FIG. 3, the gas detection element 100 can comprise a chemochromic composition 120 dispersed within a polymer matrix of a siloxane 110 (also referred to as "gas detection layer" herein) crosslinked by free radical transfer reaction with a peroxide initiator. In some elements, the resulting polymer matrix before use has a localized relative hydrogen gas presence (e.g., partial pressure) of less than the chemochromic activation threshold. In some embodiments, the resulting polymer matrix can be a pressure sensitive adhesive. In some embodiments, the element can further comprise a backing 200.

The gas detection layer may include a pressure sensitive adhesive. Furthermore, the gas detection layer may include an adhesive selected from an acrylic pressure sensitive adhesive, a silicone-based pressure sensitive adhesive, a urethane-based pressure sensitive adhesive, and a rubber-based pressure sensitive adhesive.

The PSA disclosed herein may comprise, as its base polymer, one, two or more species among acrylic polymers, rubber-based polymers, polyester-based polymers, urethane-based polymers, and silicone-based polymers.

As the acrylic polymer, for example, a polymer of a monomeric starting material comprising an alkyl (meth) acrylate as a primary monomer and possibly comprising a secondary monomer copolymerizable with the primary monomer is preferable. The primary monomer herein refers to a component that accounts for higher than 50% by weight of the monomer composition in the monomeric starting material.

The rubber-based PSA refers to a PSA comprising a rubber-based polymer as a base polymer. Examples of rubber-based polymers comprise natural rubbers, styrene-butadiene rubbers (SBR), acrylonitrile-butadiene rubbers (NBR), isoprene rubbers, chloroprene rubbers, poly-isobutyle, butyl rubbers, reclaimed rubbers and the like. These can be used singly as one species or in combination of two or more species.

In some embodiments the chemochromic activation threshold can be qualitatively be determined as the color change which indicates the presence of a reducing gas, such as hydrogen, hydrogen sulfide, carbon monoxide, methane, formaldehyde, acetylene, sulfur dioxide, ammonia, and nitrous oxide. In some embodiments, the chemochromic activation threshold can be quantitatively determined as the level of hydrogen present in the element such that when the element is exposed to a known quantity of hydrogen gas the gradient to light from dark ($\Delta L^*$) measured is greater than or equal to 5, preferably greater than or equal to 10, more preferably greater than or equal to 12. While not wanting to be bound by theory, if the level of hydrogen is above this threshold before being exposed to the known quantity of hydrogen then the $\Delta L^*$ measured will be less than what is desirable for clear indication. In some embodiments, the exposure to a known quantity of hydrogen gas can be when a representative sample of the element is immersed in about 100 vol % $H_2$ gas at about 6 mL/min flow rate in a 30 mL glass vial for about 5 minutes. For some elements, the level of hydrogen present in the element can be determined to be at or above the chemochromic activation threshold if when the element is exposed to about 100 vol % $H_2$ gas at about 6 mL/min flow rate in a 30 mL glass vial after about 5 minutes of exposure to change in gradient to light to dark ($\Delta L^*$) measured is greater than or equal to 5.

In one embodiment, the gas sensing element may further include a release liner. The release liner is provided on the side opposite to the backing of the gas sensing element.

As the release liner, conventional release paper, etc., may be used, but the release liner is not particularly limited. For example, it is possible to use a release liner having a release treatment layer on the surface of the liner substrate such as a plastic film or paper, etc., or a release liner made of a low adhesive material such as a fluorine-based polymer (polytetrafluoroethylene, etc.) or a polyolefin resin, etc. As the plastic film, a substrate made of polyethylene terephthalate (PET), polypropylene (PP), or polyethylene (PE) is preferable. The aforementioned release-treated layer may be formed by surface-treating the aforementioned liner substrate with various release treatment agents such as those that are silicone-based, long-chain alkyl-based, fluorine-based, and molybdenum sulfide, etc. When the adhesive layer is a silicone-based adhesive, a fluorosilicone-based release treatment agent is preferable, and in the case of an acrylic-based adhesive, a silicone-based release treatment agent is preferable. The thickness of the release liner is not particularly limited; however, from the viewpoint of workability, approximately less than or equal to 3 mil and greater than or equal to 0.5 mil is appropriate. The thickness of the release treating agent is not particularly limited; an appropriate thickness is 0.1 μm to 1 μm.

A. Chemochromic Composition

In some embodiments, the gas detection element can comprise a chemochromic composition. In some embodiments, the chemochromic composition can comprise one or more chemochromic elements. In some embodiments, the chemochromic composition can define a plurality of chemochromic elements, such as a powder. In some embodiments, the chemochromic composition can further comprise a chemochromic dispersant. In some embodiments, the chemochromic elements can comprise a chemochromic reagent, or pigment, that can change color as a function of concentration of at least one target gas, e.g. hydrogen gas.

The gas detection layer can include a chemochromic composition. The chemochromic composition is preferably dispersed in the gas detection layer. In this case, the gas detection performance can be exerted more preferably.

In some embodiments, the chemochromic reagent can be an irreversible sensor, changing color irreversibly in the presence of the target gas. In some embodiments, the chemochromic reagent can comprise a detection compound. In some embodiments, the chemochromic reagent can comprise a noble metal. In some embodiments, the chemochromic element can also comprise a support. In some embodiments, the detection compounds and/or noble metal can be loaded on the support. In some embodiments, the materials loaded on the support can be bonded to the support by covalent bonding, ionic bonding, metallic bonding and/or Van der Waals forces. In some embodiments, the materials loaded on the support can be bonded to the support by strong Van der Waals forces.

In some embodiments, the support can comprise a metal oxide, a metal salt, or a mixed metal. In some embodiments, the metal oxide can comprise a transition metal oxide. In some embodiments, the transition metal oxide can comprise $Al_2O_3$, $SiO_2$, $ZrO_2$, $TiO_2$, $SrTiO_3$, $AlTiO_3$, or $SrZrO_3$. In some embodiments, the transition metal oxide can comprise $TiO_2$. In some embodiments, the metal salt can comprise an alkaline earth metal salt. In some embodiments, the metal in the alkaline earth metal salt can be selected from beryllium, magnesium, calcium, strontium, barium, or radium. In some embodiments, the alkaline earth metal salt can be $BaSO_4$. In some embodiments, the alkaline earth metal salt can be $CaCO_3$. While not wanting to be limited by theory, it is thought that using divalent support material other than titania such as $BaSO_4$ or $CaCO_3$ can improve oxidation kinetics and detection sensitivity. In some embodiments, the support can comprise a mixture of a transition metal and an alkaline earth metal (e.g. $TiO_2$ and $BaSO_4$; $TiO_2$ and $CaCO_3$; and $TiO_2$, $BaSO_4$, and $CaCO_3$). While not wanting to be limited by theory, the material for the support is generally selected so that interaction of the metal particles with the surface of support surface reduces the total energy required for reduction of the detection compound so that the sensitivity of the detection compound can be increased. Such an interaction suggests a small chemical interaction between support and the metal particles allowing for the destabilization of the detection compound particles on the surface of the support by the presence of a second metal (e.g., platinum lowers the activation energy required for palladium oxide reduction). In some embodiments, the support can comprise particles having a size in a range from about 0.1 µm to about 15 µm. In some embodiments, the support particle size can range from about 0.2 µm to about 10 µm for pigment applications to maximize opacity once reacted with the target gas.

In some embodiments, the chemochromic reagent can comprise a noble metal group loaded with the detection compound on the support. In some embodiments, the detection compound can comprise a palladium based compound. In some embodiments, the palladium based compound can comprise palladium oxide, palladium hydroxide, or a palladium salt. In some embodiments, the detection compound can comprise palladium oxide. In some embodiments, the detection compound can comprise palladium hydroxide. In some embodiments, the detection compound can comprise palladium salt. In some embodiments, the detection compound can have a median size in the range of about 2 nm to about 30 nm, or about 5 nm to about 25 nm. In some embodiments, the relative weight ratio of the detection compound to the support can range from about 1:9, about 1:20, about 1:30 to about 1:200, about 1:300, or any combination thereof. In some embodiments, the relative weight ratio of the detection compound to the support can range from about 1:20 to about 1:190. In some embodiments, the mass ratio of detection compound to support can range from about 0.1 wt % to about 10 wt %. In some embodiments, the mass ratio of the detection compound to the support can range from about 0.25 wt % to about 7.5 wt %. In some embodiments, the mass ratio of the detection compound to the support can range from about 0.5 wt % to about 3.5 wt %.

In some embodiments, the chemochromic composition may be in the form of a pigment. The pigment may include carrier particles and palladium oxide supported on the surfaces of the carrier particles. Furthermore, a noble metal other than palladium may be supported or loaded on the surfaces of the carrier particles. Furthermore, the carrier particles may be titanium dioxide. In some embodiments, the noble metal material can comprise a metal, salt, or an oxide of a noble metal. In some embodiments, the noble metal material can comprise at least a metal, salt, or an oxide of a noble metal other than palladium. In some embodiments, the noble metal material can comprise gold, silver, or platinum group metals, such as platinum, iridium, osmium, rhodium, or ruthenium. In some embodiments, the noble metal material can comprise platinum. While not wanting to be limited by theory, it is thought that a palladium based oxidation catalyst such as PdO when mixed with non-palladium particles comprising a noble metal or noble metal compounds can provide an oxidation catalyst which oxidizes a reducing gas with significantly sped up oxidation kinetics and significantly increased sensitivity as compared to an oxidation catalyst of palladium (e.g., PdO) alone. In some embodiments, the noble metal material can have a median size in the range from about 2 nm to about 10 nm. In some embodiments, the mass ratio of the noble metal material to the support-with-detection compound can range from about 0.01 wt %, about 0.03 wt %, about 0.05 wt %, about 0.07 wt %, about 0.075 wt %, about 0.1 wt %, about 0.2 wt %, about 0.3 wt %, about 0.4 wt %, to about 0.5 wt %, about 0.6 wt %, about 0.7 wt %, about 0.8 wt %, about 0.9 wt %, about 1.0 wt %, or any combination thereof.

In some embodiments, the chemochromic composition can comprise between about 0.1 wt % to about 25 wt % of the total mixture before curing. The weight percentage does not include the weight of any optional backing.

In some embodiments, the chemochromic composition can comprise particles having an average size of less than 20 µm, less than 15 µm, less than 10 µm, less than 5 µm, less than 0.5 µm, or less than 0.1 µm. In some embodiments, the chemochromic composition can comprise particles having an average size of less than 10 µm.

B. Polymerized Siloxane Matrix

For some elements, the siloxane polymer matrix can be formed by curing of one or more siloxane precursors. In some embodiments, the siloxane precursors can comprise an organosiloxane. In some embodiments, the siloxane precursors can additionally comprise an oligosiloxane. In some embodiments, curing can be by crosslinking the siloxane precursors. In some embodiments, the crosslinking can be done by way of free radical transfer reaction with a treatment liquid. In some embodiments, the treatment liquid can comprise an initiator.

In some embodiments, the organosiloxane can be one or more methyl siloxanes. In some embodiments, the methyl siloxane can comprise a polymer or a monomer. In some embodiments, the methyl siloxane can comprise a polymer. In some embodiments, the methyl siloxane polymers can be linear or cyclic. Some polymer methyl siloxanes can comprise a linear polydimethyldisiloxane or a cyclic polydimethylsiloxane, such as a polydimethyl disiloxane. Some polymer methyl siloxanes can comprise a linear polymethylphenylsiloxane or a cyclic polymethylphenylsiloxane. In some embodiments, the cyclic methyl siloxane polymers can comprise the cyclomethicones such as: hexamethylcyclotrisiloxane, octamethylcyclotetrasiloxane, decamethylcyclopentasiloxane, dodecamethylcyclohexasiloxane, or combinations thereof. In some embodiments, the linear polymer methyl siloxanes can comprise the linear siloxanes such as: hexamethyldisiloxane, octamethyltrisiloxane, decamethyltetrasiloxane, dodecamethylpentasiloxane, tetradecamethylhexasiloxane, or combinations thereof. In some embodiments, the organosiloxane can comprise octamethylcyclotetrasiloxane, decamethylcyclopentasiloxane, or combinations thereof. In some embodiments, a suitable example of a polydimethylsiloxane is sold under the brand name of DOW CORNING® 282 ADHESIVE. In some embodiments, a suitable example of a polymethylphenylsiloxane is sold under the brand name of SilGrip*® PSA518, Momentive.

In some embodiments, the oligosiloxane can comprise a silicone resin. While not wanting to be limited by theory, it is thought that the silicone resin to the siloxane precursors can add tackiness to the resulting pressure sensitive adhesive. In some embodiments, the silicone resin can comprise an oligosiloxane with $Me_3SiO$ and $SiO_4$ terminal units such as an MQ resin.

In some embodiments, the treatment liquid can comprise an initiator. In some embodiments, the initiator can comprise a peroxide. Some initiators can comprise a peroxide selected from benzoyl peroxide or 2,4-dichlorobenzoyl peroxide. In some embodiments, the initiator can be a free radical initiator that initiates crosslinking between the siloxane precursor moieties. In some embodiments, the activation of the free radical initiator can result in the initiator not forming part of the covalent linkage between the moieties. In other embodiments, the activation of the free radical initiator can result in the initiator forming part of the covalent linkage between the moieties. In some embodiments, the initiator can comprise between about 0.1 wt % to about 5.0 wt % based on the weight of the siloxane precursor (silicon solids).

In some embodiments, the treatment liquid can further comprise plasticizers, which include type 1 plasticizers that can generally decrease the glass transition temperature (Tg), e.g. makes it more flexible, phthalates (n-butyl, dibutyl, dioctyl, butyl benzyl, missed esters, and dimethyl); and type 2 plasticizers that can enable more flexible, more deformable layers, and perhaps reduce the amount of voids resulting from lamination, e.g., glycols (polyethylene; polyalkylene; polypropylene; triethylene; dipropylglycol benzoate).

Type 1 plasticizers can include, but are not limited to: butyl benzyl phthalate, dicarboxylic/tricarboxylic ester-based plasticizers such as but not limited to phthalate-based plasticizers such as but not limited to bis(2-ethylhexyl) phthalate, diisononyl phthalate, bis(n-butyl)phthalate, butyl benzyl phthalate, diisodecyl phthalate, di-n-octyl phthalate, diisooctyl phthalate, diethyl phthalate, diisobutyl phthalate, di-n-hexyl phthalate and mixtures thereof; adipate-based plasticizers such as but not limited to bis(2-ethylhexyl) adipate, dimethyl adipate, monomethyl adipate, dioctyl adipate and mixtures thereof; sebacate-based plasticizers such as but not limited to dibutyl sebacate, and maleate.

Type 2 plasticizers can include, but are not limited to: dibutyl maleate, diisobutyl maleate and mixtures thereof, polyalkylene glycols such as but not limited to polyethylene glycol, polypropylene glycol and mixtures thereof. Other plasticizers which may be used include but are not limited to benzoates, epoxidized vegetable oils, sulfonamides such as but not limited to N-ethyl toluene sulfonamide, N-(2-hydroxypropyl)benzene sulfonamide, N-(n-butyl)benzene sulfonamide, organophosphates such as but not limited to tricresyl phosphate, tributyl phosphate, glycols/polyethers such as but not limited to triethylene glycol dihexanoate, tetraethylene glycol diheptanoate and mixtures thereof; alkyl citrates such as but not limited to triethyl citrate, acetyl triethyl citrate, tributyl citrate, acetyl tributyl citrate, trioctyl citrate, acetyl trioctyl citrate, trihexyl citrate, acetyl trihexyl citrate, butyryl trihexyl citrate, trimethyl citrate, alkyl sulphonic acid phenyl ester, and mixtures thereof.

In some embodiments, the treatment liquid can further comprise a solvent. In some embodiments, the solvent can comprise one or more compositions that result in a solution of siloxane precursor and initiator that is substantially blended when the siloxane precursor and the initiator are dissolved in the solvent and stirred.

C. Backing

In some embodiments, as shown in FIG. 3, the pressure sensitive adhesive gas detection element can further comprise a backing 200 (also referred to as "backing layer" herein). For some elements, the chemochromic-composition containing polymeric matrix is coated onto the backing as a layer, to form a tape. In some embodiments, the backing can be permeable to oxygen or air. In some embodiments, the backing can comprise a plant-based composition, such as cellulose, paper, cardboard, etc. In some embodiments, the backing can be a polymer-based backing. In some embodiments, the backing can comprise polyimide, polypropylene (PP), fluorinated ethylene propylene (FEP), ethylene tetrafluoroethylene (ETFE), polyethylene (PE), polytetrafluoroethylene (PTFE), perfluooroalkoxy alkanes (PFA), or polyethylene terephthalate (PET).

In some embodiments, the backing can be resistant to ultraviolet (UV) radiation. In some embodiments, the backing can further comprise an UV stabilization compound to remedy possible adverse environmental effects. In some embodiments, the UV stabilization compound can be present in the polymer matrix. In some embodiments, the UV stabilization compound can be present in both the backing and the polymer matrix. In some embodiments, the UV stabilization compound can comprise a UV absorber, a UV blocker, a hindered amine light stabilizer (HALS), or a mixture thereof. The UV blocker can comprise $ZnO_2$ or $TiO_2$. The UV absorber can comprise compounds from the triazine family, such as benzotriazol or a benzopheneone. The HALS can comprise a high molecular weight HALS (MW>1000 g/mol) or low molecular weight HALS (MW≤1000). The UV ultraviolet (UV) stabilization compound can be in the range of about 0.1 wt % to about 10 wt % as compared to the total mass of the backing.

D. Primer

Some embodiments of elements can also comprise a primer. In some embodiments, the primer can be in physical communication with the backing and the pressure sensitive adhesive matrix. While not wanting to be limited by theory, a primer can be adopted to improve the way for the pressure sensitive adhesive to "stick out" at time of cutting. In some embodiments, the primer can be compatible with the pressure sensitive adhesive matrix. In some embodiments, the primer can be compatible with phenyl-type silicone. The thickness of the primer is not particularly limited; for example, the thickness is in a range of 0.1 µm to 5 µm, and preferably in a range of 0.1 µm to 2 µm.

Here, referring back to FIG. 3, this gas detection element 100 has a feature in that the polymer matrix layer 110 of siloxane (hereinafter referred to as "gas detection layer") has sufficient adhesion.

More specifically, the gas detection layer 110 has an adhesion of greater than or equal to 0.2 N/25 mm. The adhesion is preferably greater than or equal to 1.0 N/25 mm, greater than or equal to 1.5 N/25 mm, greater than or equal to 2.0 N/25 mm, greater than or equal to 3.0 N/25 mm, or greater than or equal to 5.0 N/25 mm. The gas detection layer 110 preferably has adhesion of less than or equal to 10.0 N/25 mm.

Note that in the present embodiment, the adhesion is measured by a 180° peel strength test.

When the gas detection element 100 having the above feature is used, the gas detection layer 110 can be used as an adhesive layer. That is, by pressing the gas detection layer 110 against the measurement target, the gas detection element 100 can be adhered to the measurement target.

While not wanting to be limited by theory, it is thought that the adhesive layer can provide sufficient tack and mechanical strength to a measurement target such that when pressed against said target it can resist detachment forces and remain attached to the target.

In this case, there is no need to use, for example, an adhesive tape as a separate auxiliary tape, in order to fix the gas detection layer to the measurement target as in the conventional technology, and therefore the work efficiency can be increased. Particularly, the gas detection element 100 can be adhered to the measurement target by its own adhesion. Therefore, there is no need to use a separate fixing means.

Furthermore, in the gas detection element 100, the gas detection layer 110 can also function as an adhesive layer. Therefore, it is possible to significantly reduce problems which may occur in the conventional gas detection tape due to separately providing an adhesive layer, such as the structure becoming complicated and the measurement precision being reduced. For example, even when there is a hole in the surface of the measurement target, or when the measurement target is not planar, the gas detection layer can be appropriately fixed to the measurement target without coming off.

In this way, by way of the gas detection element 100, compared to the conventional technology, the workability of the worker can be improved when using the gas detection element 100, and additionally, it is possible to significantly reduce problems such as the structure becoming complicated and the measurement precision being reduced.

Note that in the gas detection element 100, the gas detection layer 110 may have an adhesion property with respect to the second surface of the backing 200 (in FIG. 3, the surface of the backing 200 opposite to the surface on which the gas detection layer 110 is disposed (the first surface)).

Furthermore, on the first surface or the second surface of the backing, "markings" such as a grid, scale marks, and arrows, etc., may be arranged. When the markings are a grid, the user can refer to the grid to quantitatively recognize an area where the color has changed, when the color of the gas detection element 100 changes. The grid may be a lattice in the longitudinal and transverse directions, or may be in other shapes.

The method of arranging the markings is not particularly limited. The markings may be arranged on the first surface or the second surface of the backing, for example, by printing.

The gas detection element according to an embodiment of the present invention can have the following features:

(i) Chemochromic pigment particles included in the gas detection layer that indicate an irreversible color-change reaction when exposed to reducing gas.

(ii) On a first surface of the gas detection layer, a backing material is disposed, and the backing material has a lower gas permeability with respect to the reducing gas, compared to the gas detection layer.

(iii) The gas detection layer has a thickness of 10 µm to 100 µm.

(iv) One method of application is for the gas detection element to be wound around a pipe in a manner so as to occlude a hole of the pipe. The pipe has an inner diameter of 10 mm, has both ends open, and has the hole having a diameter of 2 mm on the side surface at least in the part that directly contacts the gas. In this state, at room temperature (25° C.), the reducing gas is made to flow through from one end to the other end of the pipe for five minutes at a flow rate of 6 ml/min. Accordingly, first, the air inside the pipe is replaced by reducing gas. Subsequently, a pigment, which is inside the adhesive layer of the gas sensing element at the part covering the hole that directly contacts the gas, reacts with the gas, and the color change proceeds. The extent of the color change is that $\Delta L^*$ becomes greater than to equal to 5. Finally, in an area where $\Delta L^*$ is greater than to equal to 5, the color change is completed.

Note that the hole having a diameter of 2 mm is assumed to be a minute gas leakage portion at the joint of the pipe; for example, a leak port of a joint including a leak port. Furthermore, the reducing gas is flowing at approximately atmospheric pressure.

Conventionally, as a method of inspecting gas leakage, a method using a gas detector or soapy water has been adopted. However, according to an embodiment of the present invention, gas leakage can be inspected by a more simple and reliable method.

Note that in the present application, the "reducing gas" includes at least one of hydrogen, hydrogen sulfide, carbon monoxide, methane, formaldehyde, acetylene, sulfur dioxide, ammonia, and nitrous oxide.

The features are respectively described in detail as follows.

In the gas detection element according to an embodiment of the present invention, according to the feature of (i), once the gas detection layer contacts the reducing gas (hereinafter, also referred to as "detection gas") and the color changes, the changed color of the gas detection layer can be maintained thereafter (so-called irreversible or permanent color-change).

That is, in a case where the chemochromic pigment particles indicate a reversible reaction with respect to the detection gas, when the detection gas is no longer present around the chemochromic pigment particles, the color of chemochromic pigment particles reverses back to the original color (so-called fading phenomenon).

Therefore, in a case of reversible reaction in order to maintain the changed color, the detection gas needs to be continuously flowing and in contact with the chemochromic pigment particles. If the flow of detection gas is stopped prior to inspection, the color-change fades and hence the indicator to the location of the detection gas leak is lost.

Furthermore, in a situation where there is only a small amount of detection gas, it is difficult to maintain the changed color of the gas detection layer.

On the other hand, in the gas detection element according to an embodiment of the present invention, once the chemochromic pigment particles contact the detection gas and a color reaction occurs, the changed state is maintained thereafter. Therefore, even if a small amount of detection gas contacts the chemochromic pigment particles, the changed color can be maintained. Note that the term "irreversible" is a concept including a mode where the color changes permanently, and also an impermanent mode, that is, a mode in which a state where the color has substantially changed is maintained over a desired period of time (for example, one month).

Furthermore, the gas detection element according to an embodiment of the present invention is able to perform the measurement using a wide area of the gas detection layer, according to the feature of (ii).

That is, in the gas detection element according to an embodiment of the present invention, on a first surface of the gas detection layer, a backing material is disposed, and the backing material has a lower permeability with respect to the detection gas, compared to the gas detection layer. Therefore, the detection gas, which has entered from the second surface of the gas detection layer, can be "trapped" in the gas detection layer.

Furthermore, according to the above, even more chemochromic pigment particles included in the gas detection layer can be used for the color reaction. As a result, even more distinct color changes can be expressed.

Furthermore, the backing material may have a lower gas permeability with respect to the measurement target gas, compared to the gas detection layer. For example, the backing material may have a gas permeability that is less than or equal to 1/10 of that of the gas detection layer.

The backing material may be made of a translucent layer (or a transparent layer, the same applies hereinafter). The translucent layer preferably has flexibility.

The translucent layer may be formed of, for example, polyimide, polyethylene, fluorinated ethylene propylene copolymer (FEP), or ethylene tetrafluoroethylene copolymer (ETFE), etc.

Note that the "translucent layer" is not necessarily limited to the shape of a "layer". The "translucent layer" may be in a shape of a film, a sheet, or a plate.

Furthermore, by the gas detection element according to an embodiment of the present invention, it is possible to clearly recognize whether a color reaction has occurred, according to the feature of (iii).

That is, in an embodiment where the gas detection layer is relatively thin, and the translucent layer has a translucency as described above, even when a color reaction occurs near the second surface of the gas detection layer (i.e., the surface opposite to the surface on which the translucent layer is set) of the gas detection layer, it is possible to easily recognize the change in the color from the side of the translucent layer, that is, from the outside. Furthermore, it is possible to express the color change relatively quickly, across the entire thickness direction of the gas detection layer.

The thickness of the gas detection layer is preferably more than 5 μm, more than 10 μm, or more than 30 μm. The thickness of the gas detection layer is preferably less than 200 μm, less than 100 μm, or less than 80 μm. The thickness of the gas detection layer is preferably between 5 μm and 80 μm. Note that if the thickness is less than 5 μm, the concentration per area of the chemochromic pigment particles decreases, and the color change may not sufficiently occur in the gas detection layer.

Note that the concentration of the chemochromic pigment particles included in the gas detection layer is preferably in a range of 1 wt % to 20 wt % with respect to the entire gas detection layer, more preferably in a range of 5 wt % to 10 wt % with respect to the entire gas detection layer.

Furthermore, by the gas detection element according to an embodiment of the present invention, it is possible to clearly recognize whether a color reaction has occurred, according to the method of (iv).

The color change ($\Delta L^*$) may be greater than or equal to 5 at least in the part that directly contacts the gas. The color change ($\Delta L^*$) is preferably greater than or equal to 10 at least in the part that directly contacts the gas.

Note that the color change ($\Delta L^*$) can be evaluated by the following method.

By using a colorimeter, the chromaticity of a standard whiteboard is measured. Furthermore, the chromaticity before using the gas detection element is measured. Note that the chromaticity is expressed by the lightness index of the $L^*a^*b^*$ color system (CIELAB1976). The absolute value of the difference in the measured chromaticity between the standard whiteboard and the gas detection element before being used is obtained as $L^*_{initial}$.

Similarly, the chromaticity after using the gas detection element is measured. The absolute value of the difference in the measured chromaticity between the standard whiteboard and the gas detection element after being used is obtained as $L^*_{final}$.

From the above results, the color change ($\Delta L^*$) of the gas detection element can be evaluated by $\Delta L^* = |L^*_{final} - L^*_{initial}|$.

Furthermore, the gas sensing element according to an embodiment of the present invention may have a chroma of the color difference $\Delta C^*$ of 3 or more, before and after the color reaction.

Generally, in the $L^*a^*b^*$ display system, $L^*$ represents the lightness, and $a^*$ and $b^*$ represent the chromaticity indicating the hue and the chroma of the color. $a^*$, $b^*$ indicate the direction of color; $a^*$ corresponds to the red direction, $-a^*$ corresponds to the green direction, $b^*$ corresponds to the yellow direction, and $-b^*$ corresponds to the blue direction. As the numerical values of $a^*$ and $b^*$ increase, the color becomes brighter.

On the other hand, the $L^*C^*h$ color space is a color display system based on the $L^*a^*b^*$ color space; $L^*$ represents the lightness, and $C^*$ represents the chroma of the color. When the value of $C^*$ is high, the brightness increases, and when the value of $C^*$ is low, the color becomes dull. In general, the chroma of the color $C^*$ can be obtained by the following formula:

$$\Delta C^* = \sqrt{(a^*)^2 + (b^*)^2}$$

Furthermore, the chroma of the color difference $\Delta C^*$ is expressed by the following formula (1), where $C^*_{initial}$ is the chroma of the color of the gas sensing element before use, and $C^*_{final}$ is the chroma of the color of the gas sensing element in which the color reaction has occurred:

$$\Delta C^* = C^*_{final} - C^*_{initial} \qquad \text{formula (1)}$$

The chroma of the color difference $\Delta C^*$ is, for example, 3 or more, and preferably 5 or more. Furthermore, the chroma of the color difference $\Delta C^*$ is, for example, 100 or less, and may be 80 or less, and may be 50 or less.

Note that $\Delta C^*$ can be evaluated by the following method.

By using a colorimeter, the chromaticity of a standard whiteboard is measured. Furthermore, the chromaticity before using the gas detection element is measured. Note that the chromaticity is expressed by the lightness index of the L*C*h color system. The absolute value of the difference in the measured chromaticity between the standard whiteboard and the gas detection element before being used is obtained as $C^*_{initial}$.

Similarly, the chromaticity after using the gas detection element is measured. The absolute value of the difference in the measured chromaticity between the standard whiteboard and the gas detection element after being used is obtained as $C^*_{final}$.

From the above results, $\Delta C^*$ of the gas detection element can be evaluated by $\Delta C^* = |C^*_{final} - C^*_{initial}|$.

Here, the gas detection element according to an embodiment of the present invention may include a "diffusion part" for the detection gas on the second surface of the gas detection layer, in order to emphasize the color change.

By providing a diffusion part, it is possible to secure sufficient reaction time for the color, reaction to occur between the chemochromic pigment particles and the detection gas. Accordingly, the portion where the color changes in the gas detection layer can be enlarged, and even when the color change is weak, the color change can be easily recognized. Furthermore, minute leaks can be easily detected.

Furthermore, a leak portion (hole) of a pipe, etc., may itself have a dark color. In this case, it is often difficult for the viewer to distinguish between the color of the leak portion (hole) itself and the color change caused by the color reaction of the gas detection layer. Conversely, when a spacer is used, it is easy to distinguish between the color of the leak hole itself and the color change caused by the color reaction, and it is possible to more reliably recognize the occurrence of color change.

Alternatively, the gas detection element may be set so as to intentionally form a gap between the gas detection layer and the measurement target, to form the diffusion part. For example, the gas detection element may be set with respect to the measurement target such that a crease is formed between the gas detection layer and the measurement target, particularly in the center of the gas detection layer (not at the respective side end parts). In this case also, a gap formed by a crease, that is, a diffusion part, can be formed on the second surface of the gas detection layer.

The diffusion part may include, for example, forming a recessed part (for example, a groove part, etc.) and/or a protruding part (for example, a projection), on the second surface of the gas detection layer.

Alternatively, the diffusion part may be formed by, for example, a spacer set on the second surface of the gas detection layer. By providing such a spacer, a gap, i.e., the diffusion part can be formed relatively easily on the second surface of the gas detection layer.

The spacer may be formed by, for example, paper, an adhesive layer, a non-woven fabric, a foam, or a porous film, or a fibrous film (stitch structure or fabric structure), etc.; however, the spacer is not so limited. Furthermore, the spacer preferably has a color (for example, white) for which L* is close to 100. In this case, $\Delta L^*$ after the color change increases, and the visibility improves.

The setting form of the spacer is not particularly limited. For example, the spacer may be arranged in a planar manner on the entire second surface of the gas detection layer. Alternatively, the spacer may be arranged as a pattern on a part of the second surface of the gas detection layer. This pattern may be selected from, for example, dots, a lattice, and stripes, etc.

The thickness of the spacer may be, for example, in a range of 5 μm to 10 mm; however, the thickness of the spacer is not so limited.

By the above features, by the gas detection element according to an embodiment of the present invention, any detection gas exists, a distinct color change can be expressed in the gas detection layer.

Furthermore, according to the above, for example, even if the measurement target region is away from the inspecting staff, the inspecting staff is able to determine whether there is a color change in the gas detection element, more reliably than the conventional technology.

II. Gas Detection System

A. First Embodiment a. System Configuration

Next, a description is given of a gas detection system for visualizing gas leakage from a gas piping, etc., by attaching the above gas detection element to the gas piping, etc., and using an imaging device to remotely detect the location where the visualized gas leakage has occurred.

Figure 4:
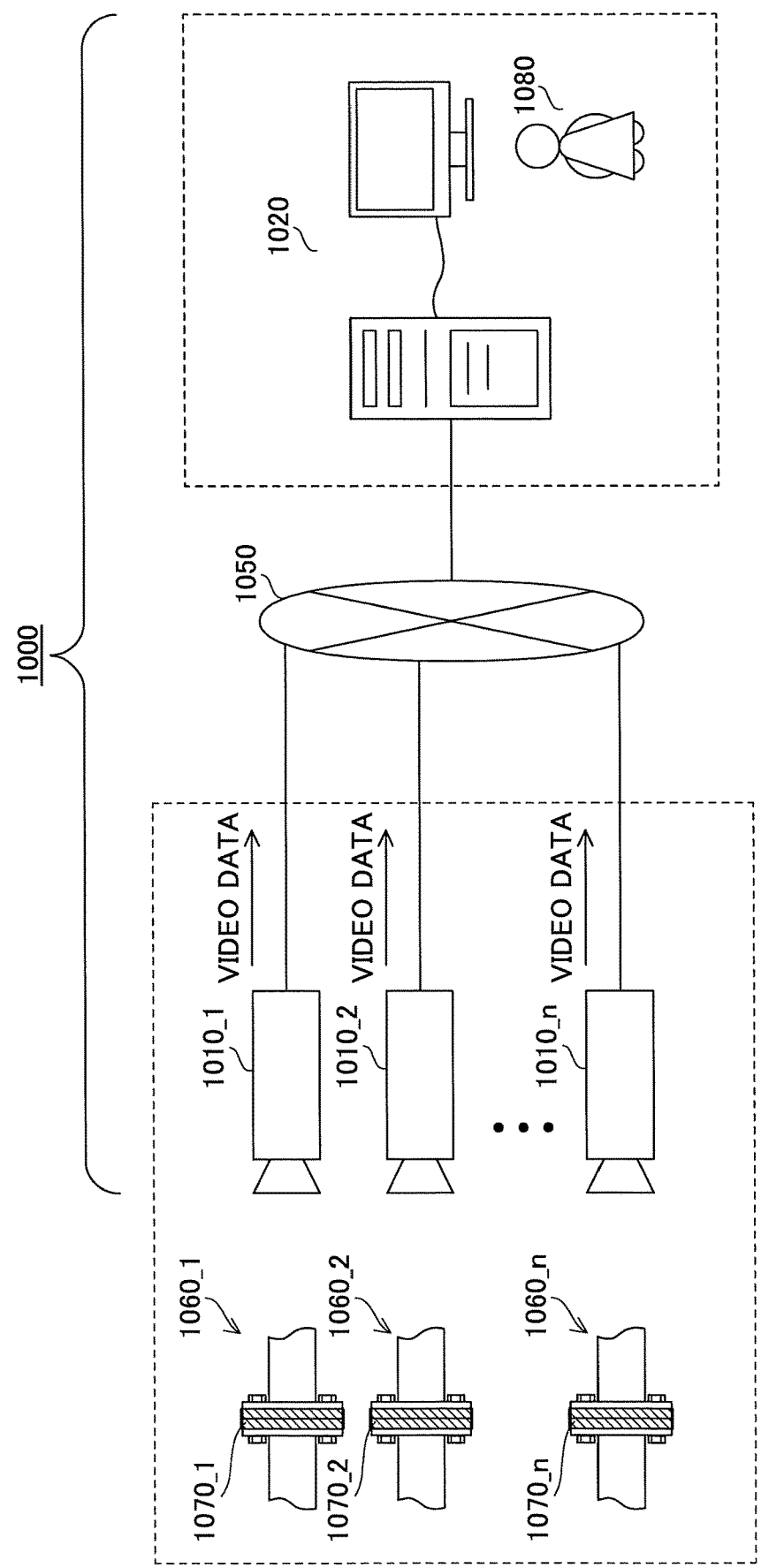
FIG. 4 is a depiction of an example of a system configuration of a gas detection system.

FIG. 4 is a depiction of an example of a system configuration of a gas detection system. As illustrated in FIG. 4, a gas detection system 1000 includes imaging devices 1010_1 to 1010_n and an information processing apparatus 1020. Note that the imaging devices 1010_1 to 1010_n and the information processing apparatus 1020 are communicably coupled to each other via a network 1050.

The imaging devices 1010_1 to 1010_n are respectively arranged near gas pipes 1060_1 to 1060_n. The imaging devices 1010_1 to 1010_n capture images of gas detection elements 1070_1 to 1070_n attached to the flange parts of the gas pipes 1060_1 to 1060_n. Furthermore, the imaging devices 1010_1 to 1010_n sequentially send the video data obtained by capturing images, to the information processing apparatus 1020. Note that the gas detection elements 1070_1 to 1070_n are attached to the flange parts because gas leakage is most likely to occur from the pipe joint part such as the flange joint or the connection joint part, or at the part of a leak port of a joint including a leak port between the device and the pipe.

The information processing apparatus 1020 is installed in a management office, etc., positioned away from the gas pipes 1060_1 to 1060_n. In the information processing apparatus 1020, a gas detection program is installed, and by executing this program, the information processing apparatus 1020 functions as a gas detection unit.

Specifically, the information processing apparatus 1020 receives video data sent from the imaging devices 1010_1 to 1010_n. Furthermore, the information processing apparatus 1020 monitors the state of the gas detection element based on the received video data, and determines whether the gas detection element has detected gas. Furthermore, when the information processing apparatus 1020 determines that the gas detection element has detected gas, the information processing apparatus 1020 displays information indicating the location where the gas leakage has occurred, etc., to an administrator 1080.

Note that the above gas detection system 1000 is particularly effective when the gas pipes 1060_1 to 1060_n are arranged at a location that is difficult for an inspection staff, etc., to access or to visually check (for example, a high place or a narrow place, on the backside, etc.).

b. Hardware Configuration of Information Processing Apparatus

Figure 5:
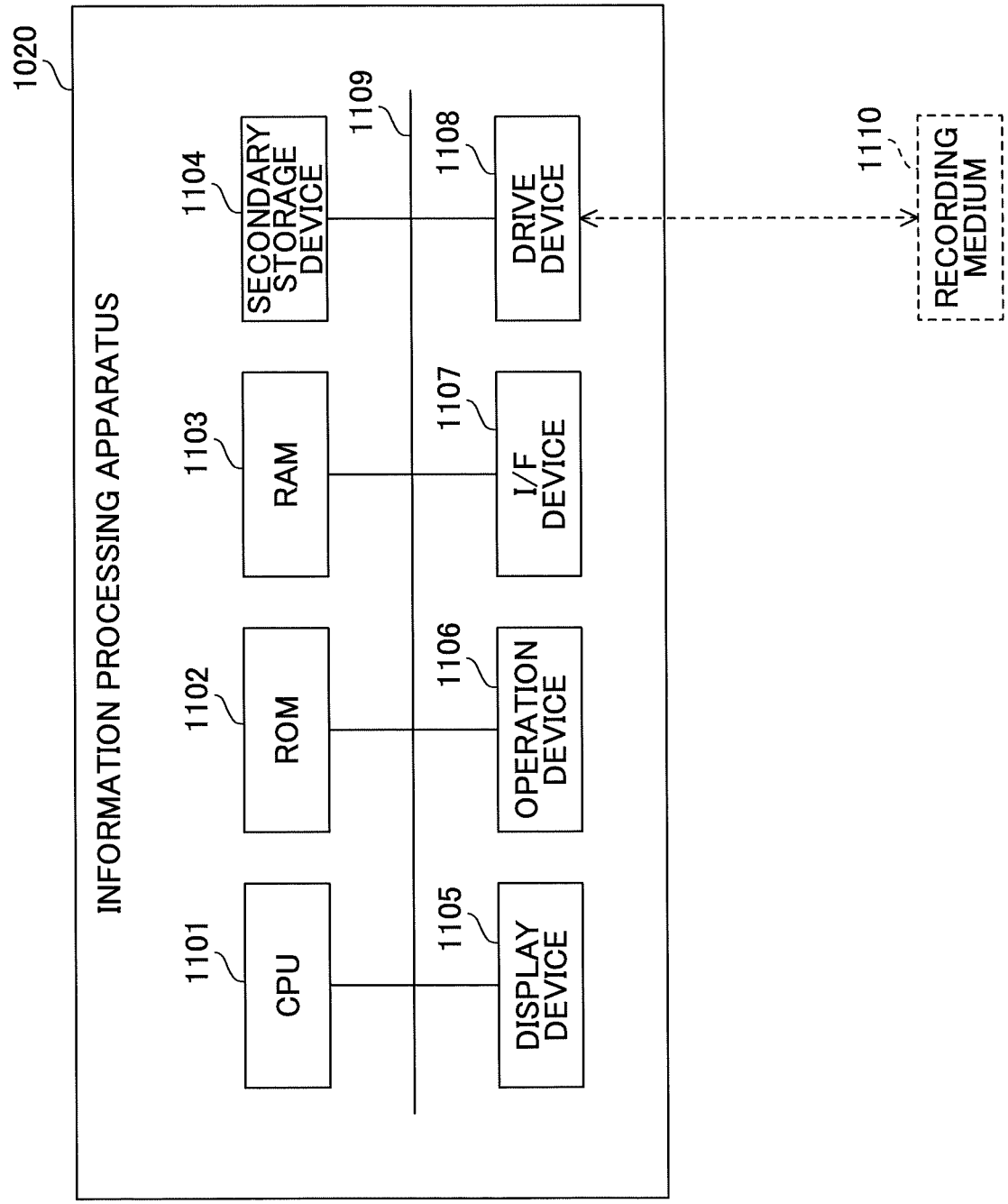
FIG. 5 is a depiction of an example of a hardware configuration of an information processing apparatus.

Next, a description is given of a hardware configuration of the information processing apparatus 1020. FIG. 5 is a depiction of an example of a hardware configuration of the information processing apparatus 1020. As illustrated in FIG. 5, the information processing apparatus 1020 includes a CPU (Central Processing Unit) 1101, a ROM (Read Only Memory) 1102, and a RAM (Random Access Memory) 1103. The CPU 1101, the ROM 1102, and the RAM 1103 form a so-called computer. Furthermore, the information processing apparatus 1020 includes a secondary storage device 1104, a display device 1105, an operation device 1106, an I/F (interface) device 1107, and a drive device 1108. Note that the respective units of the information processing apparatus 1020 are connected to each other via a bus 1109.

The CPU 1101 is a device for executing various programs (for example, a gas detection program, etc.) installed in the secondary storage device 1104.

The ROM 1102 is a non-volatile memory. The ROM 1102 functions as a main storage device for storing various programs and data, etc., needed for the CPU 1101 to execute various programs installed in the secondary storage device 1104. Specifically, the ROM 1102 stores a boot program, etc., such as a BIOS (Basic Input/Output System) and an EFI (Extensible Firmware Interface).

The RAM 1103 is a volatile memory such as a DRAM (Dynamic Random Access Memory) and a SRAM (Static Random Access Memory). The RAM 1103 functions as a main storage device for providing a work area expanded when the CPU 1101 executes various programs installed in the secondary storage device 1104.

The secondary storage device 1104 is a secondary storage device that stores various programs, information generated as the various programs are executed, and information used when the various programs are executed. The video data storage unit and the element information storage unit described below are realized in the secondary storage device 1104.

The display device 1105 is a display device for displaying information, etc., indicating the location where gas leakage has occurred, to the administrator 1080. The operation device 1106 is an input device for inputting various instructions to the information processing apparatus 1020, by the administrator 1080 of the information processing apparatus 1020. The I/F device 1107 is a connection device for connecting to the network 1050.

The drive device 1108 is a device for setting a recording medium 1110. Here, the recording medium 1110 includes media for optically, electrically, or magnetically recording information, such as a CD-ROM, a flexible disk, and a magnetic optical disk, etc. Furthermore, the recording medium 1110 may include a semiconductor memory, etc., for electrically recording information, such as a ROM and a flash memory, etc.

In the present embodiment, various programs stored in the secondary storage device 1104 are installed, for example, as the distributed recording medium 1110 is set in the drive device 1108 and various programs are read from the drive device 1108.

c. Functional Configuration of Information Processing Apparatus

Figure 6:
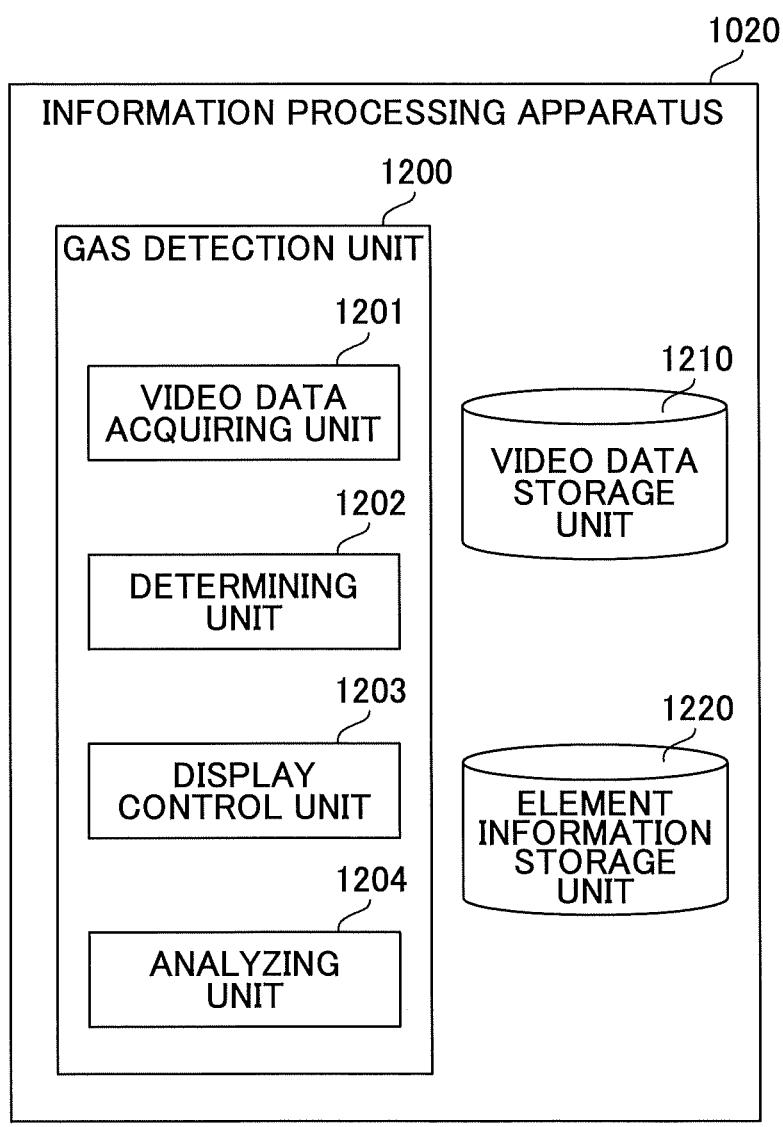
FIG. 6 is a depiction of an example of a functional configuration of an information processing apparatus.

Next, a description is given of a functional configuration of the information processing apparatus 1020. FIG. 6 is a depiction of an example of a functional configuration of the information processing apparatus 1020. As described above, the information processing apparatus 1020 has the gas detection program installed, and as this program is executed, the information processing apparatus 1020 functions as a gas detection unit 1200.

The gas detection unit 1200 includes a video data acquiring unit 1201, a determining unit 1202, a display control unit 1203, and an analyzing unit 1204.

The video data acquiring unit 1201 receives video data sent from the imaging devices 1010_1 to 1010_n, and stores the video data in a video data storage unit 1210 in association with time information indicating the recording date and the recording time.

The determining unit 1202 reads the video data stored in the video data storage unit 1210 in units of frames, and monitors the state of the gas detection element included in each frame. Note that the determining unit 1202 monitors, as the state of the gas detection element, for example, the change of color, the shape of the area where the color has changed, the size of the area where the color has changed, and the patterns in the area where the color has changed, the color density and changes in the hue, etc.

Furthermore, the determining unit 1202 determines whether the gas detection element has detected gas, based on the results of monitoring the gas detection element. Furthermore, when the determining unit 1202 determines that the gas detection element has detected gas, the determining unit 1202 refers to an element information storage unit 1220, reads information relevant to the corresponding gas detection element (including information indicating the position of the corresponding gas detection element), and reports the information to the display control unit 1203. Furthermore, the determining unit 1202 reports the video data at the time when the determining unit 1202 determines that the gas detection element has detected gas, to the display control unit 1203.

Furthermore, the determining unit 1202 records history information, which indicates that the determining unit 1202 has determined that the gas detection element has detected gas, in the video data storage unit 1210 in association with the video data.

When the display control unit 1203 receives a report of information relevant to the gas detection element from the determining unit 1202, and further receives a report about the video data at the time when the gas detection element has detected the gas, the display control unit 1203 displays a management screen (a screen for reporting the gas leakage) on the display device 1105.

The analyzing unit 1204 acquires, as analysis information, the video data, time information, and element information, etc., associated with the history information indicating that the determining unit 1202 has determined that the gas detection element has detected gas, among the video data stored in the video data storage unit 1210, and analyzes the acquired analysis information. For example, the analyzing unit 1204 calculates the cycle at which the gas leakage occurs based on the acquired information, and estimates the location and the time or the leakage amount when the gas leakage is highly likely to occur next.

d. Description of Video Data Stored in the Video Data Storage Unit

Next, a description is given of video data stored in the video data storage unit 1210. FIG. 7 is a depiction of an example of video data stored in the video data storage unit

1210. As illustrated in FIG. 7, video data 1300 includes the information items of "imaging device name" and "attribute information".

In the "imaging device name", a name of an imaging device identifying the imaging devices 1010_1 to 1010_n is stored. In the "attribute information", information indicating the attributes (for example, the installation position, the resolution, and the frame rate, etc.) of the imaging devices 1010_1 to 1010_n is stored.

Furthermore, as illustrated in FIG. 7, the video data, which is sent from the imaging devices 1010_1 to 1010_n, is stored in association with time information at a position corresponding to each of the imaging device names. Each of a plurality of dotted-line blocks in FIG. 7 indicates video data, which has been recorded by the imaging device having the corresponding imaging device name at the corresponding date and time.

Note that among the dotted-line blocks, a black-filled dotted-line block indicates that the video data is associated with history information indicating that the determining unit 1202 has determined that the gas detection element has detected gas.

e. Description of Element Information Stored in Element Information Storage Unit Next, a description is given of element information stored in the element information storage unit 1220. FIG. 8 is a depiction of an example of element information stored in the element information storage unit 1220. As illustrated in FIG. 8, element information 1400 includes the information items of "identification number", "gas detection element type", "attachment location", "attachment component", "attachment time", and "attachment worker".

In the "identification number", the identification number for identifying the gas detection element is stored. In the "gas detection element type", information indicating the type of the gas detection element is stored. In the "attachment location", information for identifying the pipe to which the gas detection element is attached is stored. In the "attachment component", information for identifying the component to which the gas detection element is attached is stored.

In the "attachment time", information indicating the time when the gas detection element has been attached to the attachment component is stored. In the "attachment worker", information for identifying the worker who attached the gas detection element to the attachment component is stored.

f. Specific Example of Process Executed by Units of Gas Detection Unit

Next, a description is given of specific examples of processes executed by the determining unit 1202 and the display control unit 1203, among the specific examples of processes executed by the units of the gas detection unit 1200.

(1) Specific Example of Determination Process by Determining Unit

First, a description is given of a specific example of a determination process by the determining unit 1202. FIGS. 9 to 12 are depictions of a specific example of a determination process by the determining unit 1202. Among these, the reference numerals 1501 to 1703 in FIGS. 9 to 11 indicate how the state of the gas detection element has changed in various forms, during the time $t_1$ to time $t_3$, in the video data obtained by recording the gas detection element attached to the flange of the pipe. Furthermore, in FIG. 12, 1801 indicates the state of the gas detection element at the time $t_1$, in the video data obtained by recording the gas detection element attached to the flange of the pipe.

Figure 9:
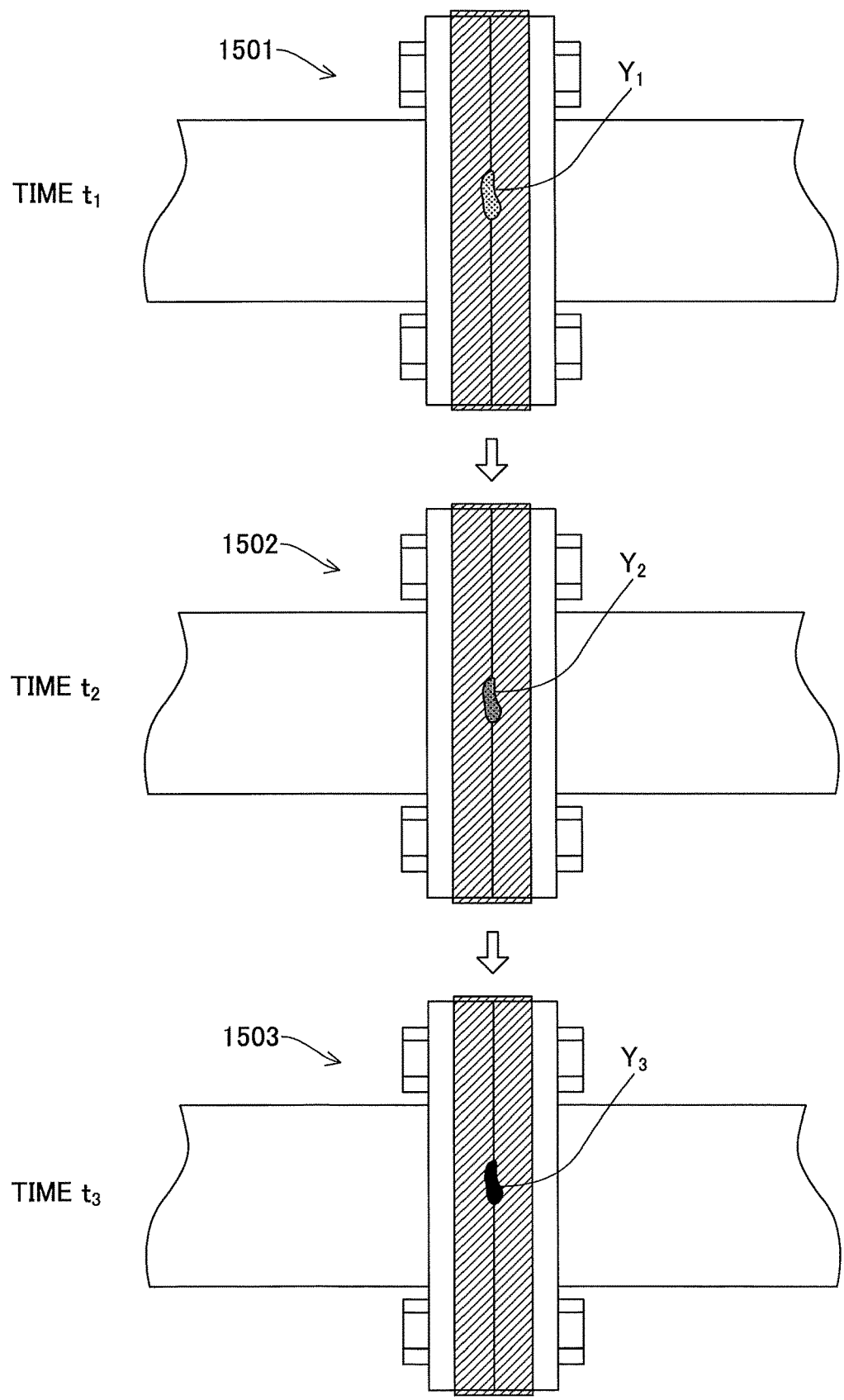
FIG. 9 is a depiction of a specific example of a determination process by a determining unit.

More specifically, the reference numerals 1501 to 1503 of FIG. 9 indicate that the color of an area in part of the gas detection element has changed during the time $t_1$ to time $t_3$, as the gas detection element has contacted gas. When the state of the gas detection element has changed in this manner, for example, the determining unit 1202 calculates the average luminance values $Y_1$, $Y_2$, and $Y_3$ of the area having a different color from other areas at the respective times. Furthermore, when the calculated average luminance value becomes greater than or equal to a predetermined threshold, the determining unit 1202 determines that the gas detection element has detected gas. Alternatively, when the variation in the average luminance value per unit time (for example, $(Y_3-Y_2)/(t_3-t_2)$) becomes greater than or equal to a predetermined threshold (for example, a value corresponding to $\Delta L^*=5$) during the time $t_1$ to time $t_3$, the determining unit 1202 determines that the gas detection element has detected gas.

Figure 10:
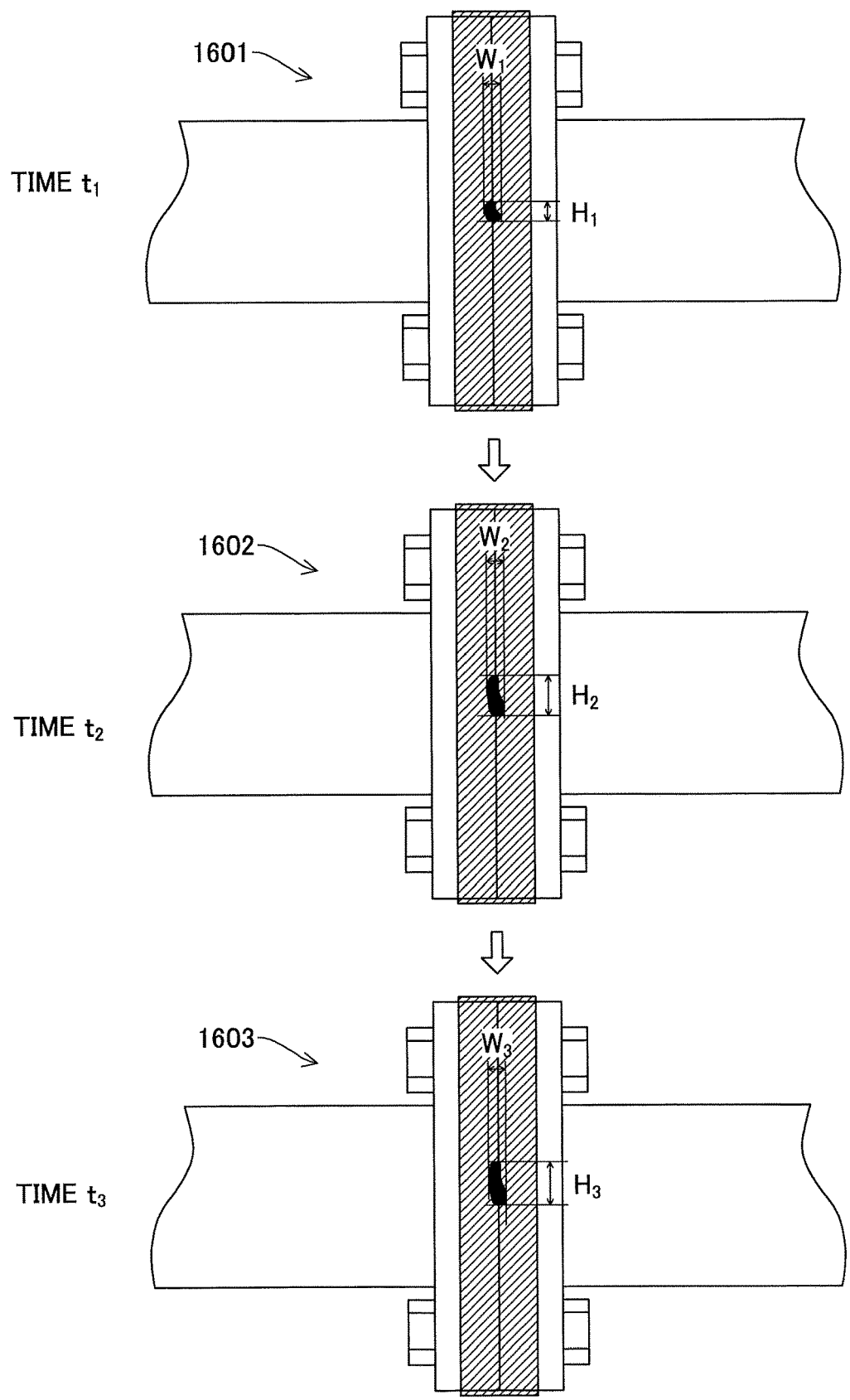
FIG. 10 is a depiction of a specific example of a determination process by a determining unit.

The reference numerals 1601 to 1603 of FIG. 10 indicate that the shape of an area in the gas detection element has changed during the time $t_1$ to time $t_3$, as the gas detection element has contacted gas. When the state of the gas detection element has changed in this manner, for example, the determining unit 1202 calculates the ratio of the width and height of the area where the color has changed $H_1/W_1$, $H_2/W_2$, and $H_3/W_3$ at the respective times. Furthermore, when the calculated ratio of the width and height becomes greater than or equal to a predetermined threshold, the determining unit 1202 determines that the gas detection element has detected gas. Alternatively, when the variation in the ratio per unit time (for example, $(H_1/W_1-H_2/W_2)/(t_1-t_2)$) becomes greater than or equal to a predetermined threshold during the time $t_1$ to time $t_3$, the determining unit 1202 determines that the gas detection element has detected gas.

Figure 11:
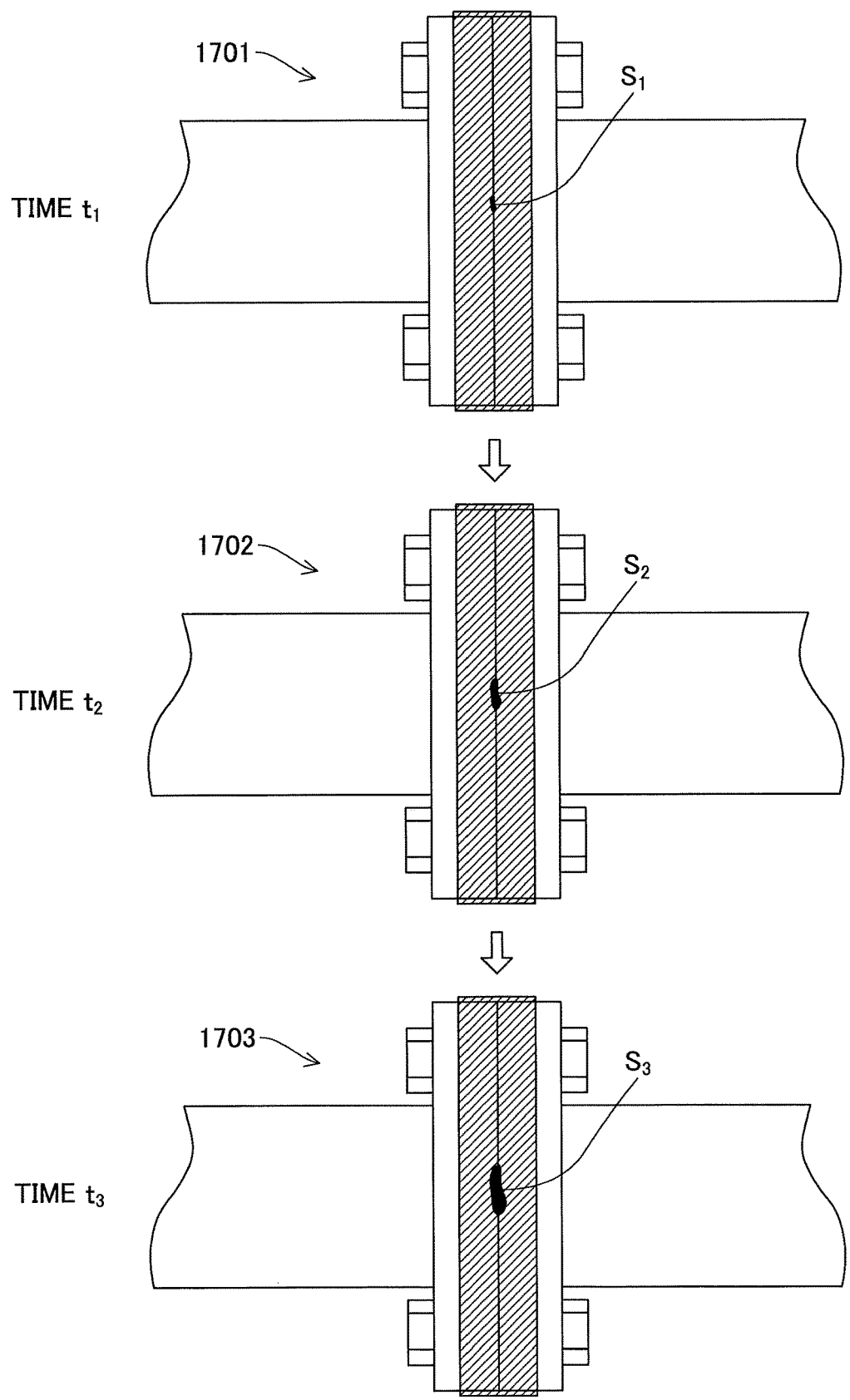
FIG. 11 is a depiction of a specific example of a determination process by a determining unit.

The reference numerals 1701 to 1703 of FIG. 11 indicate that the size of an area where the color has changed in the gas detection element has changed during the time $t_1$ to time $t_3$, as the gas detection element has contacted gas. When the state of the gas detection element has changed in this manner, for example, the determining unit 1202 calculates the sizes $S_1$ to $S_3$ of the area where the color has changed at the respective times. Furthermore, when the calculated size becomes greater than or equal to a predetermined threshold, the determining unit 1202 determines that the gas detection element has detected gas. Alternatively, when the variation in the size per unit time (for example, $(S_1-S_3)/(t_1-t_3)$) becomes greater than or equal to a predetermined threshold during the time $t_1$ to time $t_3$, the determining unit 1202 determines that the gas detection element has detected gas.

Figure 12:
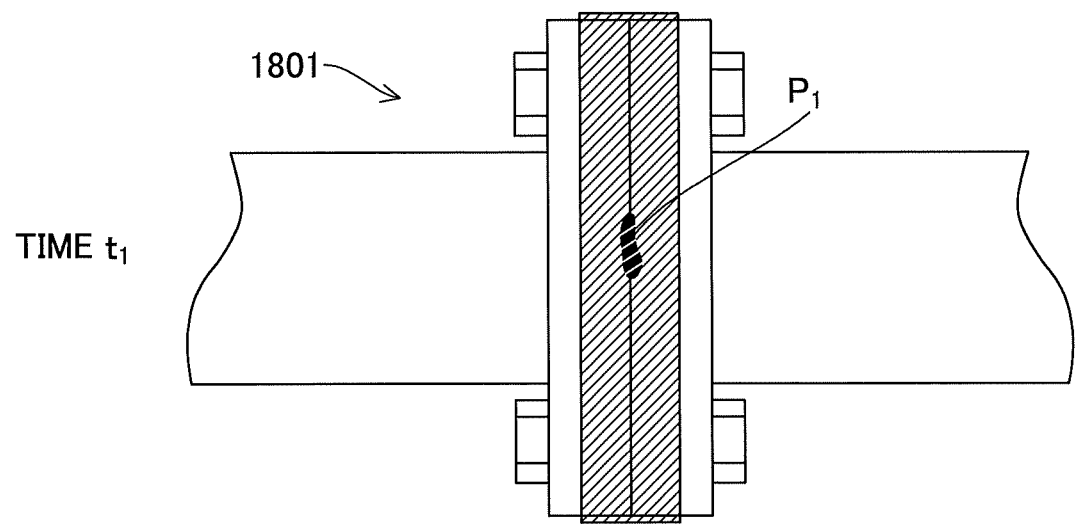
FIG. 12 is a depiction of a specific example of a determination process by a determining unit.

The reference numeral 1801 of FIG. 12 indicates that the color of the gas detection element has changed and a predetermined pattern (for example, a stripe pattern) has been formed, as the gas detection element, which has been subjected to pattern processing, has contacted gas. When the state of the gas detection element has changed in this manner, for example, the determining unit 1202 calculates the similarity with a predetermined pattern, and when the calculated similarity becomes greater than or equal to a predetermined threshold, the determining unit 1202 determines that the gas detection element has detected gas.

As described above, by recording the gas detection element that changes in color when contacting gas, and determining the change in the state of the gas detection element in various manners, it is possible to precisely determine that the gas detection element has detected gas. As a result, according to the present embodiment, the occurrence of gas leakage can be remotely detected.

(2) Management Screen Displayed by Display Control Unit

Figure 13:
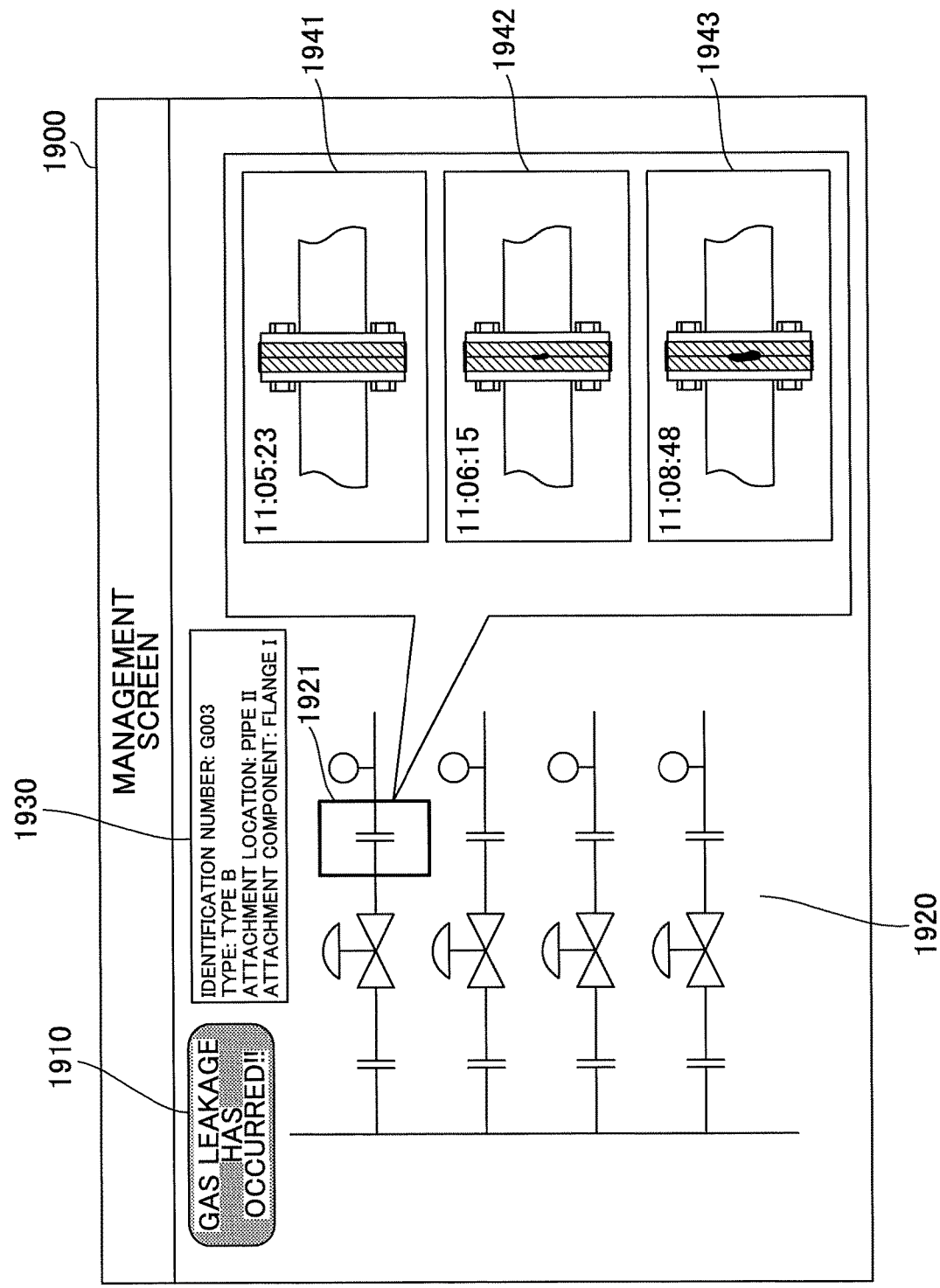
FIG. 13 is a depiction of an example of a management screen displayed by a display control unit.

Next, a description is given of a specific example of a management screen displayed by the display control unit 1203. FIG. 13 is a depiction of an example of a management screen displayed by the display control unit 1203. As illustrated in FIG. 13, a management screen 1900 includes a message 1910 indicating that gas leakage has occurred. Furthermore, the management screen 1900 includes a pipe system drawing 1920 for indicating the location where the gas leakage has occurred, and a rectangular block 1921 indicating the gas detection element that has detected gas.

Furthermore, the management screen 1900 includes information 1930 regarding the gas detection element that has detected gas, among the records in the element information 1400. Furthermore, the management screen 1900 includes video data items 1941 to 1943 within a predetermined time range including the timing at which the determining unit 1202 has determined that the gas detection element has detected gas, among the video data items in the video data 1300.

As described above, when the gas leakage has occurred, by displaying the location where the gas leakage has occurred on the management screen 1900, it is possible to remotely identify the location where the gas leakage has occurred, according to the present embodiment.

g. Flow of Gas Detection Process by Gas Detection Unit

Figure 14:
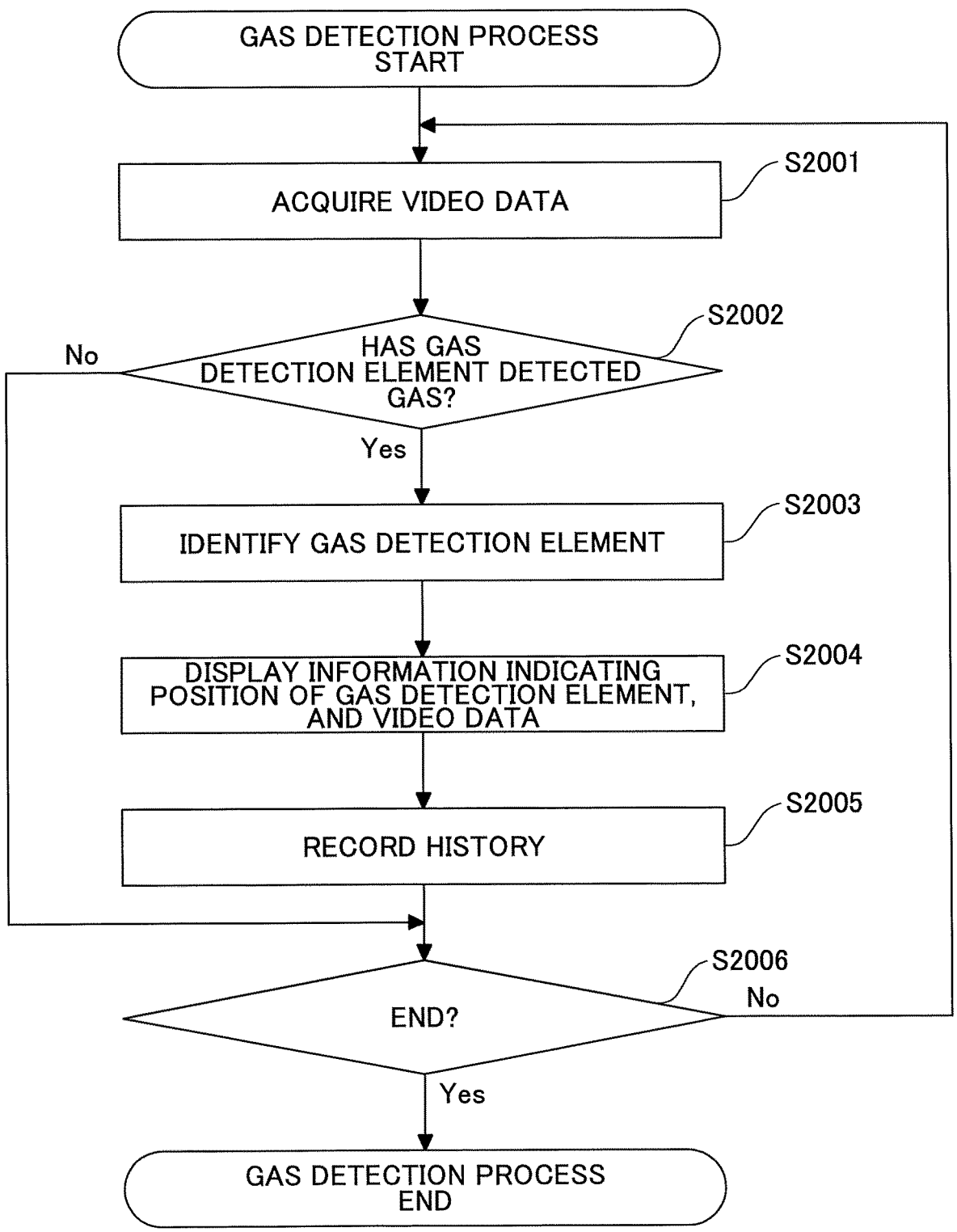
FIG. 14 is a flowchart of a flow of a gas detection process.

Next, a description is given of a flow of the gas detection process by the gas detection unit 1200. FIG. 14 is a flowchart of a flow of a gas detection process by the gas detection unit 1200. When the attachment of the gas detection elements has been completed and the imaging devices 1010_1 to 1010_n start recording, the gas detection unit 1200 starts to execute the gas detection process illustrated in FIG. 14.

In step S2001, the video data acquiring unit 1201 acquires video data sent from the imaging devices 1010_1 to 1010_n, and stores the video data in the video data storage unit 1210 in association with time information.

In step S2002, the determining unit 1202 reads the video data from the video data storage unit 1210, and monitors the states of the gas detection elements. Furthermore, the determining unit 1202 determines whether any of the gas detection elements have detected gas, based on the monitoring results.

In step S2002, when the video data storage unit 1210 determines that none of the gas detection element has detected gas (NO in step S2002), the process proceeds to step S2006. On the other hand, in step S2002, when the video data storage unit 1210 determines that a gas detection element has detected gas (YES in step S202), the process proceeds to step S2003.

In step S2003, the determining unit 1202 refers to the element information storage unit 1220 and identifies the gas detection element that has detected gas.

In step S2004, the determining unit 1202 reports, to the display control unit 1203, the information relevant to the gas detection element identified in step S2003 (including information indicating the position of the gas detection element), among the information in the element information storage unit 1220. Furthermore, the determining unit 1202 reports, to the display control unit 1203, the video data of a predetermined time range including the timing when the determining unit 1202 has determined that the gas detection element has detected gas. Accordingly, the display control unit 1203 can display, on the management screen 1900, the information relevant to the gas detection element and the video data at the time when the gas detection element has detected gas.

In step S2005, the determining unit 1202 records history information indicating that the determining unit 1202 has determined that the gas detection element has detected gas, in the video data storage unit 1210 in association with the video data.

In step S2006, the video data acquiring unit 1201 determines whether to end the gas detection process. In step S2006, when the video data acquiring unit 1201 determines not to end the gas detection process (NO in step S2006), the process returns to step S2001. On the other hand, in step S2006, when the video data acquiring unit 1201 determines to end the gas detection process (YES in step S2006), the gas detection process is ended.

h. Overview

As can be clearly seen from the above descriptions, the gas detection system 1000 according to the first embodiment of the present invention has the following features:

Includes an imaging device that records changes in a gas detection element that can visualize gas leakage by changing in color when contacting gas, and that sends the video data obtained by recording the gas detection element.

Monitors the state of the gas detection element based on the video data sent from the imaging device, and determines whether the gas detection element has detected gas based on the monitoring results.

When it is determined that the gas detection element has detected gas, the gas detection system 1000 communicates information of the location where the gas leakage has occurred, to a management screen to be displayed.

Accordingly, the gas detection system 1000 according to the present embodiment can remotely detect that gas leakage has occurred, and identify the location where the gas leakage has occurred.

B. Second Embodiment

In the first embodiment described above, the location where gas leakage has occurred is displayed to the administrator 1080 via the management screen 1900; however, the target of reporting the location where gas leakage has occurred is not limited to the administrator 1080.

For example, the gas detection system may search for an inspecting staff who is near the location where gas leakage has occurred, and the location where gas leakage has occurred may be displayed on a mobile terminal held by the inspection staff, to report the location to the inspection staff.

Furthermore, in the first embodiment, the information about the gas detection element that has detected gas is reported to the administrator 1080; however, the purpose of the information about the gas detection element is not limited to reporting to the administrator 1080.

For example, the attachment component to which the gas detection element is attached, may be identified from the information about the gas detection element that has detected gas, and a process of placing orders to replace the attachment component may be performed based on the information.

Figure 15:
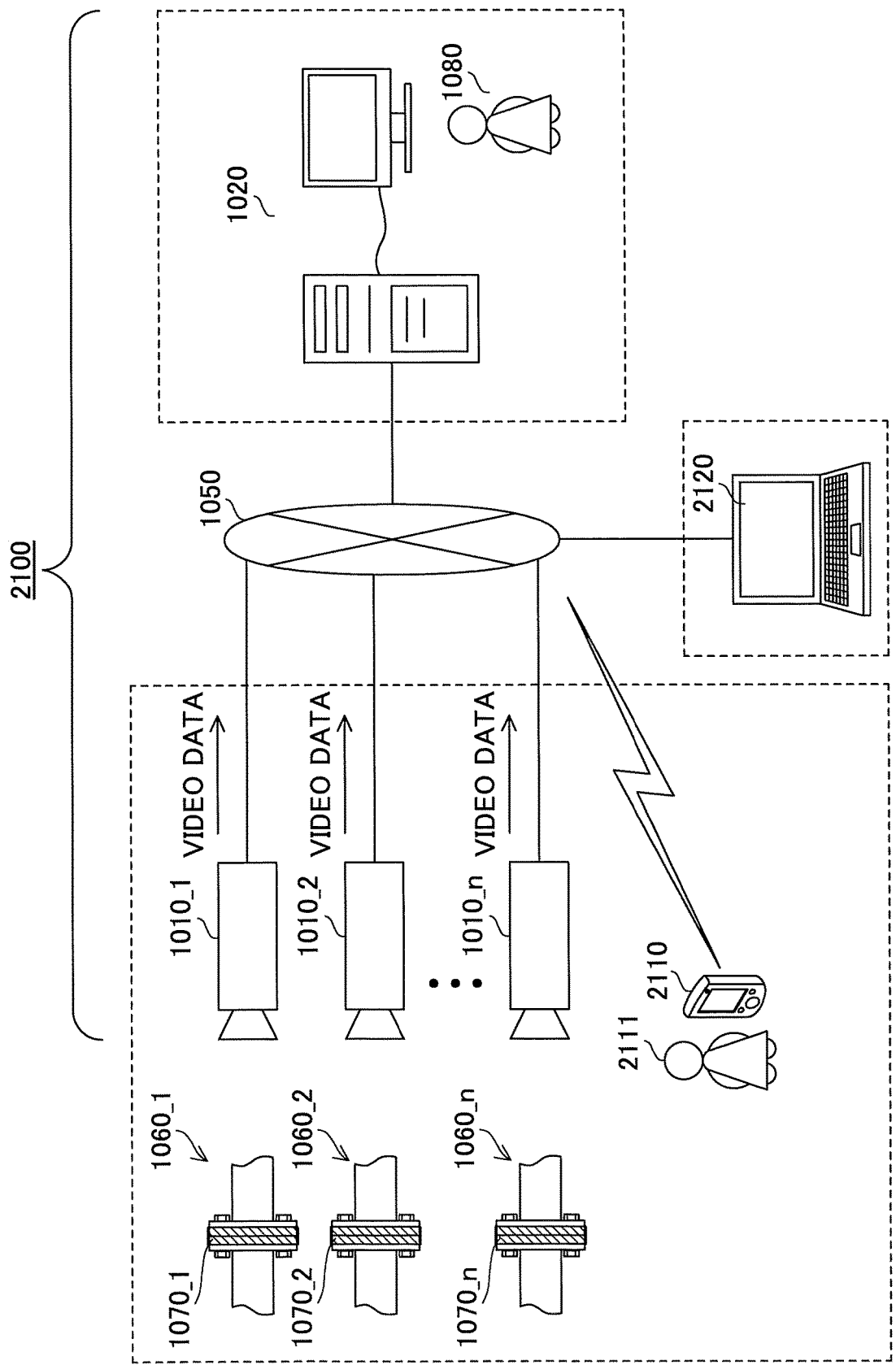
FIG. 15 is a depiction of an example of a system configuration of another gas detection system.

FIG. 15 is a depiction of an example of system configuration of another gas detection system. As illustrated in FIG. 15, a gas detection system 2100 includes a mobile terminal 2110 held by an inspecting staff, and a terminal 2120 for placing orders for the attachment component, in addition to the elements of the gas detection system 1000 described with reference to FIG. 4 in the first embodiment.

The mobile terminal 2110 receives information indicating the location where gas leakage has occurred from the information processing apparatus 1020, and displays the received information.

The terminal 2120 receives information for placing an order for the attachment component, from the information processing apparatus 1020, and places an order for the attachment component.

As described above, by connecting with the mobile terminal 2110 and the terminal 2120, etc., via the network 1050, the gas detection system 2100 can provide various services to business offices that manufacture and use various kinds of gas.

C. Other Embodiments

In the first and second embodiments, one imaging device is arranged with respect to one gas detection element; however, one imaging device may be arranged with respect to a plurality of gas detection elements. Alternatively, a plurality of imaging devices may be arranged with respect to one gas detection element.

Furthermore, in the above embodiments, the type of imaging device is not particularly described; however, the imaging device may be an imaging device that can capture images of a visible light region, an imaging device that can capture images of an infrared ray region, or an imaging that can capture images of an ultraviolet region. For example, an imaging device that can capture images of an ultraviolet ray region can visualize an invisible flame (for example, a hydrogen flame), and therefore it is possible to quickly discover a fire break-out. Alternatively, the imaging device may be a photoelectric sensor having a white LED light source. In the case of a photoelectric sensor, for example, it is preferable that each color component of RGB can be detected by a detection distance=30 to 500 [mm], a spot size=3 to 20 [mm], and a response time=200 [psec].

Furthermore, in the above embodiments, all of the video data sent from the imaging device is stored in the video data storage unit 1210; however, only the video data within a predetermined time range including the timing at which that the determining unit 1202 has determined that the gas detection element has detected gas, may be stored.

Furthermore, in the above embodiments, a plurality of examples of forms for determining the change of the state of the gas detection element are described; however, these forms may be used in combination. Furthermore, a form other than the forms given as examples in the above embodiments may be used to determine change in the state of the gas detection element.

Furthermore, in the above embodiments, it is determined as to whether the gas detection element has detected gas by making a comparison with a predetermined threshold; however, the determination method is not so limited. For example, the determination may be made by performing pattern matching with a known variation pattern.

Furthermore, in the above embodiments, the determination is made based on video data; however, the determination may be made by combining data other than video data. Examples of data other than video data are any kind of monitoring data needed for monitoring the state of the gas detection element, such as data relevant to the brightness in the surroundings (for example, illumination data, data indicating the weather, and data indicating the time), etc. Therefore, the output device for outputting the monitoring data is not limited to the imaging device described above, but may be another kind of output device for outputting data other than video data.

Furthermore, in each of the above-described embodiments, at the timing when it is determined that the gas sensing element has detected gas, information indicating that gas leakage has occurred is displayed on the management screen 1900. However, the method of displaying information on the management screen 1900 is not so limited. For example, when the color change of the gas sensing element is reversible, and the flow of gas in the gas pipe is shut off or other gas flows into the gas pipe, the color of the gas sensing element may to return to the color before changing. In this case, even though the cause of the gas leakage has not been improved, the administrator 1080 may erroneously recognize that the cause of the gas leakage has been improved.

In view of such a case, once the determining unit 1202 determines that the gas sensing element has detected the gas, a detection flag may be turned ON until there is input from the administrator 1080 that the cause of the gas leakage has been improved. Furthermore, the display control unit 1203 may display information indicating that there is a possibility of gas leakage on the management screen 1900, while the detection flag is ON. Thus, it is possible to eliminate the possibility that the administrator 1080 erroneously recognizes that the cause of the gas leakage is improved.

III. Method for Producing a Pressure Sensitive Gas Detection Adhesive.

Figure 16:
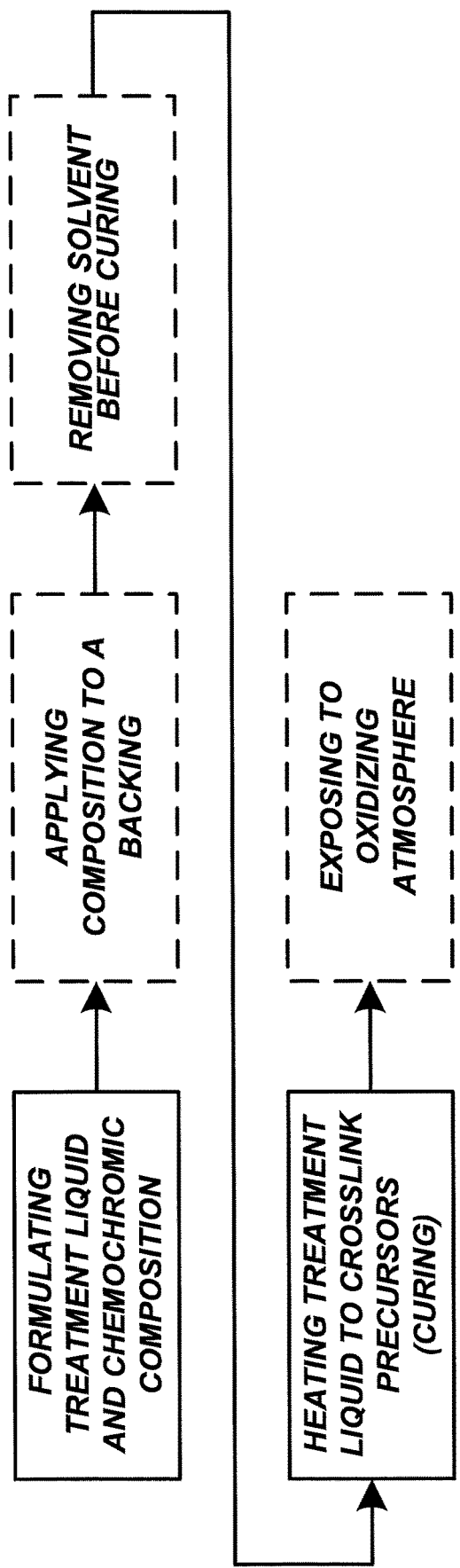
FIG. 16 is a depiction of one possible methodology for fabricating a gas detection element.
Figure 17:
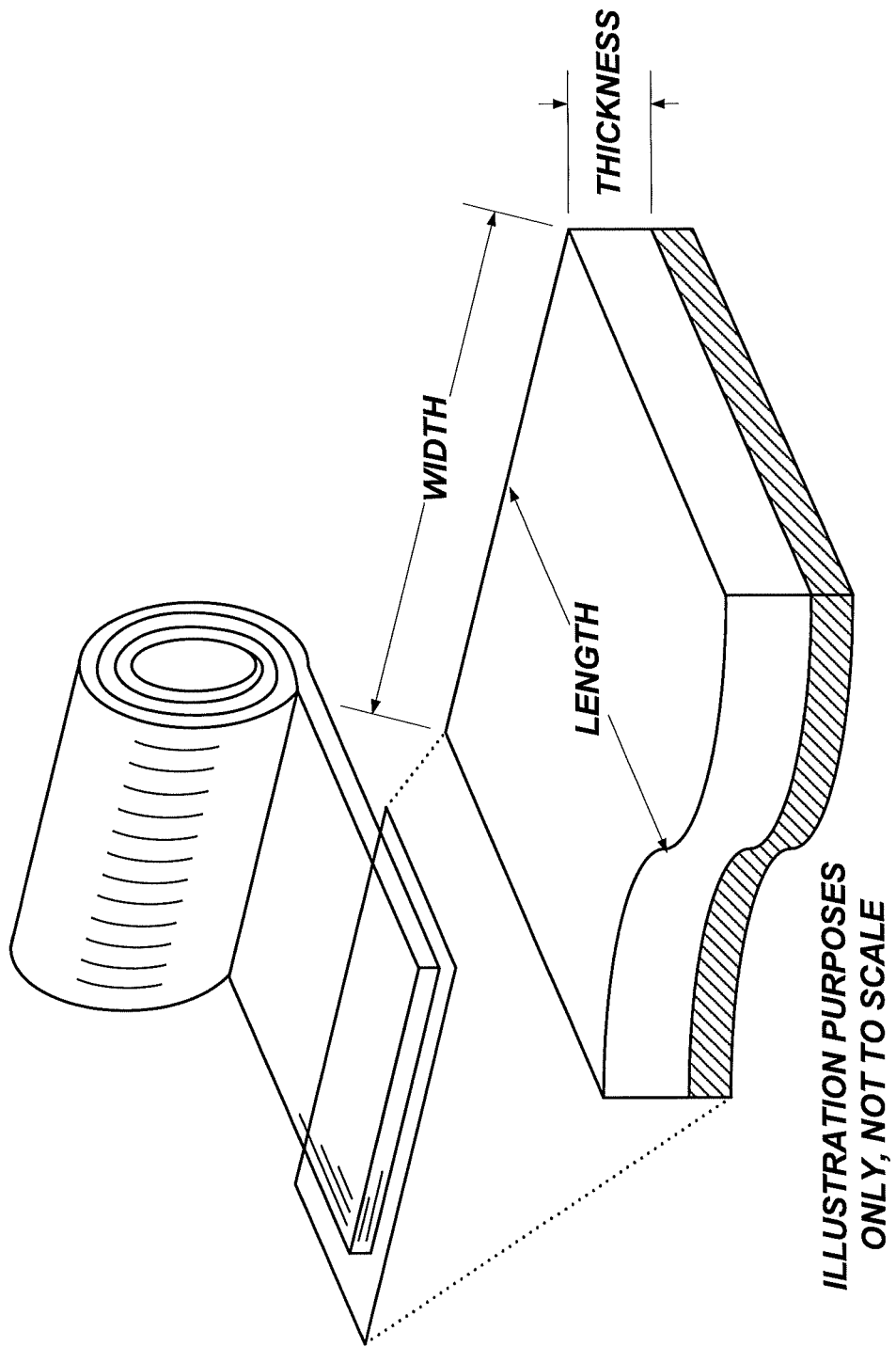
FIG. 17 is a schematic of the coordinate reference for thickness, width, and length of the pressure sensitive adhesive layer.

A method of producing a pressure sensitive gas detection adhesive can be described, such as the one shown in FIG. 16. The method may comprise: (1) formulating a treatment liquid and a chemochromic composition, the treatment liquid comprising a siloxane precursor and an initiator; and (2) heating the treatment liquid to a temperature sufficient to activate the initiator so that the precursor is crosslinked to create a polymer matrix containing the chemochromic composition, where the polymer matrix can have a localized hydrogen gas presence less than the threshold for activating the chemochromic composition. In some embodiments, the resulting polymer matrix can be a pressure sensitive adhesive.

For some methods, formulating a treatment liquid and a chemochromic composition can comprise mixing the treatment liquid and the chemochromic composition.

In some embodiments, the chemochromic composition can comprise one or more chemochromic elements. In some embodiments the chemochromic composition can define a plurality of chemochromic elements, such as a powder. In some embodiments, the chemochromic elements are the same afore-described elements. In some chemochromic compositions, the chemochromic composition can further comprise a dispersant for the chemochromic elements. In some embodiments, the dispersant can comprise methyl ethyl ketone. In some embodiments, the chemochromic composition can comprise between about 0.1 wt % to about 25 wt % of the total mixture before curing. The weight percentage does not include the weight of any optional backing. In some embodiments, the chemochromic composition can comprise about 1 wt %, about 3 wt %, about 5 wt % about 10 wt %, about 10.8 wt %, about 11.1 wt %, or about 15.0 wt % of the total mixture before curing.

In some embodiments, the siloxane polymer matrix can be formed by curing, or crosslinking, of one or more siloxane precursors. In some embodiments, the treatment liquid can comprise a siloxane precursor and an initiator. In some embodiments, the siloxane precursors can comprise an organosiloxane. In some embodiments, the siloxane precursors can additionally comprise an oligosiloxane. In some embodiments, curing can be by crosslinking the siloxane precursors. In some embodiments, the crosslinking can be done by way of free radical transfer reaction within the treatment liquid.

In some embodiments, the organosiloxane can be one or more methyl siloxanes. In some embodiments, the methyl siloxane can comprise a polymer or a monomer. In some embodiments, the methyl siloxane can comprise a polymer. In some embodiments, the methyl siloxane polymers can be linear or cyclic. Some polymer methyl siloxanes can comprise a linear polydimethyldisiloxane or a cyclic polydimethylsiloxane. Some polymer methyl siloxanes can comprise a linear polymethylphenylsiloxane or a cyclic polymethylphenylsiloxane. In some embodiments, the cyclic polymer methyl siloxanes can comprise a cyclomethicone such as: hexamethylcyclotrisiloxane, octamethylcyclotetrasiloxane, decamethylcyclopenta-siloxane, dodecamethylcyclohexasiloxane, or combinations thereof. In some embodiments, the linear polymer methyl siloxanes can comprise a linear siloxane such as: hexamethyldisiloxane, octamethyltrisiloxane, decamethyltetrasiloxane, dodecamethylpentasiloxane, tetradecamethylhexasiloxane, or combinations thereof. In some embodiments, the siloxane precursor can comprise octamethylcyclotetrasiloxane, decamethylcyclopentasiloxane, or combinations thereof.

In some embodiments, the oligosiloxane can comprise a silicone resin. While not wanting to be limited by theory, it is thought that the silicone resin to the siloxane precursors can add tackiness to the resulting pressure sensitive adhesive. In some embodiments, the silicone resin can comprise an oligosiloxane with $Me_3SiO$ and $SiO_4$ terminal units such as an MQ resin.

For some methods, the initiator can comprise a peroxide. In some embodiments, the initiator can comprise an initiator selected from benzoyl peroxide or 2,4-dichlorobenzoyl peroxide. In some embodiments, the initiator can comprise between about 0.1 wt % to about 5.0 wt % based on the weight of the siloxane precursor (silicon solids).

In some embodiments, the treatment liquid can further comprise a solvent. In some embodiments, the solvent can comprise one or more compositions that result in a solution of siloxane precursor and initiator that is substantially blended when the siloxane precursor and the initiator are dissolved in the solvent and stirred. In some embodiments, the solvent can comprise an alkylbenzene such as: methyl benzene, ethyl benzene, etc. In some embodiments, the methyl benzene can be selected from xylene or toluene. In some embodiments, xylene can comprise 1,2-dimethylbenzene (o-xylene), 1,3-dimethylbenzene (m-xylene), 1,4-dimethylbenzene (p-xylene), or any combination thereof.

In some embodiments, the heating step can further comprise the additional step of removing any solvent from the treatment liquid before heating the treatment liquid to activate the initiator. In some embodiments, to remove the solvent from the treatment liquid, the liquid can be heated at a temperature range from about 25° C. to 100° C. For example, in the case of 25° C., the heating time is preferably approximately 10 minutes, and in the case of 100° C., the heating time is preferably approximately 30 seconds.

In some embodiments, heating the treatment liquid to a temperature sufficient to activate the initiator can comprise heating to a temperature sufficient for curing, or analogously for the initiator to cause crosslinking between the siloxane precursor moieties. In some embodiments, heating to a temperature sufficient to activate the initiator can comprise heating the treatment liquid at a temperature from 120° C. to 200° C., for 1 to 3 minutes.

In some methods, there can be the additional step of applying the formulated treatment liquid and chemochromic composition on a backing. In some embodiments, the applying the formulated treatment liquid and chemochromic composition can be in the form of a layer to form a tape. In some embodiments, applying the formulated treatment liquid and chemochromic composition is done before heating.

In some embodiments, the backing can be a polymeric backing. In some embodiments, the backing can be a polymer-based backing. In some embodiments, the polymer-based backing can comprise polyimide, fluorinated ethylene propylene (FEP), ethylene tetrafluoroethylene (ETFE), polyethylene (PE), polytetrafluoroethylene (PTFE), perfluoroalkoxy alkanes (PFA), or polyethylene terephthalate (PET). In some embodiments, the backing can be resistant to UV radiation.

In some embodiments, applying the contacted treatment liquid and chemochromic composition can be done by methods known by those skilled in the art for creating a layer of desired thickness, such as, by film coating, bar coating, blade coating, spray coating, dip coating, die coating, spin coating, etc. In some embodiments, the application is done by film coating. In some embodiments, the contacted treatment liquid and chemochromic composition can be coated to form a layer with a post-cure thickness of between about 5 μm to about 200 μm, or about 25 μm, 30 μm, 45 μm, 60 μm, or 85 μm.

For some methods, the method can further comprise the step of exposing the polymer matrix to an oxygen-containing atmosphere. While not wanting to be limited by theory, it is believed that the trace amounts of elemental hydrogen created during matrix crosslinking can be blocked from attaching to active sites in the chemochromic composition by the increased presence of elemental oxygen in the surrounding atmosphere, which in turn permeates the polymer matrix blocking the chemochromic reagent's active sites. In some embodiments, exposing oxygen-containing atmosphere can comprise an exposing to air. In some embodiments, exposing to an oxygen-containing atmosphere can comprise exposing to a gas with at least 10 vol % oxygen gas, at least 15 vol % oxygen gas, at least 20.95 Vol % oxygen gas, at least 30 vol % oxygen gas, or at least 40 vol % oxygen gas. In some embodiments, the step of exposing the polymer matrix to an oxygen-containing atmosphere can comprise maintaining the physical dimensions of the pressure sensitive adhesive material to less than an amount sufficient to allow contact of the resulting pressure sensitive adhesive to the oxygen-containing atmosphere. In some embodiments, the step of exposing the polymer matrix to an oxygen-containing atmosphere can comprise a combination of backing material selection for permeability and maintaining the physical dimensions of the pressure sensitive adhesive material.

In some embodiments, exposing the polymer matrix to an oxygen-containing atmosphere can comprise using a release liner that may be permeable to an oxygen-containing atmosphere.

In some embodiments, using a release liner can comprise using a liner that is permeable to oxygen. In some steps, using a release liner may comprise using a liner that is permeable to air. In some embodiments, using a permeable release liner can comprise using a liner that can comprise a plant-basedor plastic film which is permeable to air and/or oxygen, such as cellulose, paper, cardboard, polyethylene terephthalate (PET), polyethylene (PE), polypropylene (PP), etc.

In some embodiments, the backing can be a polymeric backing. In some embodiments, the backing can be a polymer-based backing. In some embodiments, the polymer-based backing can comprise polyimide (Nylon), fluorinated ethylene propylene (FEP), ethylene tetrafluoroethylene (ETFE), polyethylene (PE), polytetrafluoroethylene (PTFE), perfluoroalkoxy alkanes (PFA), or polyethylene terephthalate (PET). In some embodiments, the backing can be resistant to UV radiation.

EXAMPLES

Example 1.1: Compound/Mixture Formulation

Fabrication of the Chemochromic Elements (0.3 wt % Pt on a 3.0 wt % PdO/TiO$_2$ Support).

Depositing PdO on TiO$_2$:

To deposit PdO, a slurry of 2.5 g TiO$_2$ (<5 µm size, rutile, Sigma Aldrich) in 100 mL of DI water was adjusted to pH 10.6 using a NaOH solution (12M solution from pure pellets and DI water, EMD Millipore) and stirred at 70° C. for one hour. Then, 2.50 mL of PdCl$_2$ solution (0.281 M in 2 M HCl, Aldrich) was added dropwise to the mixture, taking care to keep the solution at pH 10.6 using a NaOH solution (12 M sol., EMD Millipore). Once all the PdCl$_2$ solution was added, the pH of the mixture was then adjusted to 8 using HCl (3 M, Aldrich). The mixture was then stirred and heated for one hour while the PdO was deposited onto the surfaces of the titania supports. The resulting solid PdO/TiO$_2$ particulates were then filtered, washed thoroughly with DI water and dried at 110° C. for 3 hours, to yield a solid, compound #1 (C-1) of 3.3 wt % PdO.

Pt Loading:

Then, to give a loading of about 0.3 wt % Pt on the support, 0.019 g Na$_2$PtCl$_6$.6H$_2$O (Aldrich) was added to a slurry of 2.5 g C-1 suspended in 100 mL of ethanol (Aldrich). The pH of the resulting solution was then adjusted to 6 using NaOH (12 M sol., EMD Millipore). Sonication was then carried out on the reaction mixture using a direct immersion titanium tip ultrasonic homogenizer set at 20 kHz, 100 W·cm$^{-2}$ (Omni-ruptor 4000, Omni International, Inc.) at room temperature. The resulting product was filtered, thoroughly washed with ethanol (Aldrich), and then dried at room temperature. Then, the product was baked at 110° C. for 3 hours to provide chemochromic elements of 0.26 wt % Pt, or CC-1.

Example 2.1: Element formulation

Fabrication of Gas Detection Element #1.

Creating the Coating Mixture:

The treatment liquid was created by adding benzoyl peroxide (1.115 g, 97%, Luperox® A98, Aldrich) to toluene (10.0 g, Aldrich), stirring the resulting solution for 1 minute to fully dissolve the benzoyl peroxide. Then the resulting solution and toluene (16.92 g, Aldrich) were all added to pressure sensitive adhesive precursor (72.1 g, DOW CORNING® 282 ADHESIVE) and stirred by hand for 3 minutes to form a treatment liquid. A chemochromic composition was created by dispersing CC-1 (2.29 g) in methyl ethyl ketone (15 g, Aldrich) making sure to break up any large chunks to create a dispersion. The chemochromic composition was then added to the treatment liquid and mixed by hand until uniform, about 3 minutes. The result was a coating mixture.

Coating the Pressure Sensitive Adhesive on the Backing:

The resulting coating mixture was then film coated using bar applicator, (SA-210, Baker-Type-Applicator, Tester Sangyo Co., Ltd.) on a 30 cm×40 cm polyimide backing (1 mil, 100 PST Kapton, Dupont High Performance Films) with the dial set to the desired pressure sensitive adhesive thickness. The coating mixture was placed in front of the applicator and the applicator was then pulled across the backing coating it as it progressed. The result was a coated backing.

Removing Solvent and Curing Pressure Sensitive Adhesive:

The coated backing was then air dried at 25° C. for 30 seconds to remove the solvent. Next, the coated backing was then cured in an oven at 177° C. for 3 minutes. The result was a pressure sensitive adhesive gas detection element (GDE-1).

Example 2.2: Element formulation

Fabrication of Additional Gas Detection Elements.

Additional gas detection elements were synthesized using methods similar to those used in Example 2.1 with the exception of the changes outlined in Table 1. Additional materials used were: pressure sensitive adhesive (SilGrip*® PSA518, Momentive), fluorinated ethylene propylene (FEP) backing (2 mil, 200C FEP100/Teflon, Dupont High Performance Films), polyethylene (PE) backing (1 mil, S1113, Uline), and polyethylene terephthalate (PET) (2 mil, PET/Lumirror S10 Toray Plastics). For the embodiments with the polyethylene (PE) backing, the pressure sensitive adhesive solution was coated on a fluoro carbon treated PET liner (2 mil Clear Polyester "S Take off", Loparex, Cary N.C.) for heat treatment and then subsequently laminated on the PE film because the PE film did not have high heat resistance.

TABLE 1

Characteristics of Gas Detection Elements.

| Element | Mass Quantities (g) | | | | | PSA Material | Backing Material | Adhesive Thick. (µm) |
| | CC-1 | MEK | BPO | Toluene | PSA | | | |
| --- | --- | --- | --- | --- | --- | --- | --- | --- |
| GDE-1 | 2.29 | 15.0 | 0.96 | 26.9 | 72.1 | Dow 282 | 1 Mil PI/Kapton | 30 |
| GDE-2 | 2.29 | 15.0 | 0.96 | 26.9 | 72.1 | Dow 282 | 1 Mil PI/Kapton | 60 |
| GDE-3 | 2.29 | 15.0 | 0.96 | 26.9 | 72.1 | Dow 282 | 1 Mil PI/Kapton | 85 |
| GDE-4 | 2.29 | 15.0 | 0.48 | 26.9 | 72.1 | Dow 282 | 1 Mil PI/Kapton | 85 |
| GDE-5 | 2.29 | 15.0 | 0.24 | 26.9 | 72.1 | Dow 282 | 1 Mil PI/Kapton | 85 |
| GDE-6 | 2.29 | 15.0 | 0.0 | 26.9 | 72.1 | Dow 282 | 1 Mil PI/Kapton | 85 |
| GDE-7 | 2.29 | 15.0 | 0.96 | 26.9 | 72.1 | Dow 282 | 2 Mil FEP/Teflon | 30 |

TABLE 1-continued

Characteristics of Gas Detection Elements.

| Element | Mass Quantities (g) | | | | PSA | PSA Material | Backing Material | Adhesive Thick. (μm) |
| | CC-1 | MEK | BPO | Toluene | PSA | | | |
|---|---|---|---|---|---|---|---|---|
| GDE-9 | 2.29 | 10.4 | 1.0 | 28.0 | 75.0 | Mom. PSA518 | 1 Mil PI/Kapton | 30 |
| GDE-10 | 2.29 | 10.4 | 1.0 | 28.0 | 75.0 | Mom. PSA518 | 1 Mil PI/Kapton | 60 |
| GDE-11 | 2.29 | 10.4 | 1.0 | 28.0 | 75.0 | Mom. PSA518 | 1 Mil PI/Kapton | 85 |
| GDE-12 | 2.29 | 10.4 | 1.0 | 28.0 | 75.0 | Mom. PSA518 | 2 Mil FEP/Teflon | 30 |
| GDE-13 | 2.29 | 10.4 | 1.0 | 28.0 | 75.0 | Mom. PSA518 | 2 Mil FEP/Teflon | 30 |
| GDE-14 | 2.29 | 10.4 | 1.0 | 28.0 | 75.0 | Mom. PSA518 | 1 Mil PE | 30 |
| GDE-15 | 2.29 | 10.4 | 1.0 | 28.0 | 75.0 | Mom. PSA518 | 1 Mil PET/Mylar | 30 |
| GDE-16 | 1.70 | 7.7 | 1.0 | 28.0 | 75.0 | Mom. PSA518 | 1 Mil PI/Kapton | 30 |
| GDE-17 | 1.87 | 8.5 | 1.0 | 28.0 | 75.0 | Mom. PSA518 | 1 Mil PI/Kapton | 20 |
| GDE-18 | 1.87 | 8.5 | 1.0 | 28.0 | 75.0 | Mom. PSA518 | 1 Mil PI/Kapton | 40 |
| GDE-19 | 2.29 | 10.4 | 1.0 | 28.0 | 75.0 | Mom. PSA518 | 1 Mil PI/Kapton | 15 |
| GDE-20 | 2.29 | 10.4 | 1.0 | 28.0 | 75.0 | Mom. PSA518 | 1 Mil PI/Kapton | 45 |
| GDE-21 | 2.71 | 12.3 | 1.0 | 28.0 | 75.0 | Mom. PSA518 | 1 Mil PI/Kapton | 20 |
| GDE-22 | 2.71 | 12.3 | 1.0 | 28.0 | 75.0 | Mom. PSA518 | 1 Mil PI/Kapton | 40 |
| GDE-23 | 2.88 | 13.1 | 1.0 | 28.0 | 75.0 | Mom. PSA518 | 1 Mil PI/Kapton | 30 |
| GDE-24 | 2.29 | 10.4 | 1.0 | 28.0 | 75.0 | Mom. PSA518 | 2 Mil Acrylic/UVA | 30 |

Comparative Example 2.1: Comparative Elements

Fabrication of Comparative Element #1.

Creating Treatment Liquid: The treatment liquid was created by adding benzoyl peroxide (1.115 g, 97%, Luperox® A98, Aldrich) to one part of a two-part gas permeable acrylic (100 g, ORIBAIN BPS4891TX, Toyo Ink) and stirred by hand for 3 minutes to form a treatment liquid. A chemochromic composition was created by dispersing CC-1 (2.29 g) in methyl ethyl ketone (15 g, Aldrich) making sure to break up any large chunks to create a dispersion. The chemochromic composition was then added to the treatment liquid and mixed by hand until uniform, about 3 minutes. The result was a coating mixture.

Coating the Pressure Sensitive Adhesive on the Backing:

The resulting coating mixture was then film coated using bar applicator (SA-210, Baker-Type-Applicator, Tester Sangyo Co., Ltd.) on a 30 cm×40 cm polyimide backing (1 mil, Kapton, Dupont) with the dial set to the desired wet pressure sensitive adhesive thickness. The coating mixture was placed in front of the applicator and the applicator was then pulled across the backing coating it as it progressed. The result was a coated backing.

Removing Solvent and Curing Pressure Sensitive Adhesive:

The coated backing was then air dried at 25° C. for 30 seconds to remove the solvent. Next, the coated backing was then cured in an oven at 177° C. for 3 minutes. The result was a comparative gas detection element (CGDE-1).

Comparative Example 2.2: Comparative Elements

Fabrication of Additional Comparative Elements

Additional comparative gas detection elements were fabricated using a method similar to those in Comparative Example 2.2 with the exception of the change outlined in Table 2.

TABLE 2

Characteristics of the Comparative Gas Detection Elements.

| Element | Mass Quantities (g) | | | | PSA | PSA Material | Backing Material | Adhesive Thick. (μm) |
| | CC-1 | MEK | BPO | Toluene | PSA | | | |
|---|---|---|---|---|---|---|---|---|
| CGDE-1 | 2.53 | 15.0 | 1.12 | — | 100.0 | Toyo 4891TX | 1 Mil PI/Kapton | 30 |
| CGDE-2 | 2.53 | 15.0 | 1.12 | — | 100.0 | Toyo 4891TX | 1 Mil PI/Kapton | 60 |

TABLE 2-continued

Characteristics of the Comparative Gas Detection Elements.

| | Mass Quantities (g) | | | | PSA | Backing | Adhesive Thick. |
|---------|------|------|-----|---------|-------|----------------|----------------|----------|
| Element | CC-1 | MEK | BPO | Toluene | PSA | Material | Material | (μm) |
| CGDE-3 | 2.53 | 15.0 | 1.12 | — | 100.0 | Toyo 4891TX | 1 Mil PI/Kapton | 85 |
| CGDE-4 | 2.53 | 15.0 | 1.12 | — | 100.0 | Toyo 4891TX | 2 Mil FEP/Teflon | 30 |

Example 3.1: Characterization of Experimental Results

Characterization of Premature Reactivity.

All gas detection elements were qualitatively assessed to determine the possibility of premature color-change due to the reaction of the chemochromic composition with residual radicals in the polymer matrix of the pressure sensitive adhesive. The embodiments were examined immediately after curing with a color analyzer (PCM+, ColorTec, Clinton, N.J. USA). When required, the color analyzer was calibrated with a standard white panel included with the unit. In addition, some embodiments were also exposed to a UV accelerated exposure conditions and their color was measured afterwards. The results are presented in Table 3. In general, it is shown that trace amounts of radicals appear to be coming from the free radical transfer reaction generated by benzoyl peroxide initiator. When the amount of benzoyl peroxide initiator decreases below adequate levels, there appears to be less hydrogen chemochromic activation. In general, for all embodiments, the results show that trace amounts of radicals due to crosslinking can pre-activate the chemochromic composition in larger dimension polymer matrices as seen by comparing CGDE-3, which has a thickness of 85 microns versus CGDE-1, which has a thickness of 30 microns, or CGDE-2, which has a thickness of 60 microns. While not wanting to be limited by theory, it is thought that the ability of air (oxygen) to permeate the polymer matrix prevents radical reaction on active sites of chemochromic reagent and makes the chemochromic reagent's active sites less susceptible to false indications. However, in thicker geometries the air (oxygen) adsorption in the center of the material is slow and results in the activation of the chemochromic reagent. It was also noted that the presence of ultraviolet radiation may lead to the creation of trace radical in the matrix, causing premature chemochromic activation.

Test results of UV exposure showed the possibility of premature chemochromic activation by radicals that were generated in the backing layer. Silicone, polyimide, and FEP have inherent UV resistance. Acrylic adhesive does not have UV resistance and when exposed to UV, it generates radicals. Polyimide stops UV in its layer. Sample CGDE-1 did not show premature color change because UV was stopped by polyimide. FEP does not stop UV, although fluoro carbon polymer itself is stable under UV. Regarding sample CGDE-4, UV passed through FEP and reacted with acrylic adhesive, generating radicals and causing premature chemochromic activation. Regarding sample GDE-15, PET backing reacted with UV and generated radicals. These radicals moved and prematurely activated the chemochromic pigment in the silicone adhesive layer (i.e. the gas detection layer). As a result, premature color change was observed even though the silicone adhesive has UV resistance. GDE-24 has PET film backing that contains a UV absorber (2 mil PET, Toray Lumirror U-65V) and it did not release radicals into the silicone adhesive layer. Radicals were absorbed by the UV absorber. As a result, there was no premature color change of GDE-24.

As shown here, UV resistant backing (where radicals are not generated when the backing is exposed to UV) is necessary to be used for this gas sensing element.

It is well known that fluoro carbon polymer films are stable against UV, but are not capable of stopping UV.

The same results would be expected with other fluoro carbon polymer films like PFA (tetra fluoro ethylene per fluoro alkylvivyl ether copolymer), ETFE (tetra fluoro ethylene hexa fluoro ethylene copolymer), and PTFE (poly tetra fluoro ethylene).

It is well known that HALS (Hindered Amine Light Stabilizers) also has radical scavenging properties.

Regarding GDE-14, premature color change was not observed with PE backing in this test.

Polyethylene does not have a functional group or unsaturated bonding and hence it is relatively strong against UV.

TABLE 3

Shelf Performance of Select Gas Detection Elements during Curing and during UV-Irradiation.

| Element | Initiator (BPO) | PSA Material | Backing Material | Adhesive Thick. (μm) | Chemochromic activation at curing | Chemochromic activation during UV Exposure |
|---------|-----------------|--------------|------------------|----------------------|------------------------------------|---------------------------------------------|
| CGDE-1 | 1.12 g | Toyo 4891TX | 1 Mil PI/Kapton | 30 | ○ | ○ (backing) |
| CGDE-2 | 1.12 g | Toyo 4891TX | 1 Mil PI/Kapton | 60 | ○ | — |
| CGDE-3 | 1.12 g | Toyo 4891TX | 1 Mil PI/Kapton | 85 | ● | — |
| CGDE-4 | 1.12 g | Toyo 4891TX | 2 Mil FEP/Teflon | 30 | ○ | ● (backing) |
| GDE-1 | 0.96 g | Dow 282 | 1 Mil PI/Kapton | 30 | ○ | ○ (backing) |
| GDE-2 | 0.96 g | Dow 282 | 1 Mil PI/Kapton | 60 | ● | — |
| GDE-3 | 0.96 g | Dow 282 | 1 Mil PI/Kapton | 85 | ● | — |

TABLE 3-continued

Shelf Performance of Select Gas Detection Elements during Curing and during UV-Irradiation.

| Element | Initiator (BPO) | PSA Material | Backing Material | Adhesive Thick. (μm) | Chemochromic activation at curing | Chemochromic activation during UV Exposure |
|---|---|---|---|---|---|---|
| GDE-4 | 0.48 g | Dow 282 | 1 Mil PI/Kapton | 85 | ◐ | — |
| GDE-5 | 0.24 g | Dow 282 | 1 Mil PI/Kapton | 85 | ○ | — |
| GDE-6 | 0 g | Dow 282 | 1 Mil PI/Kapton | 85 | ○ | — |
| GDE-7 | 0.96 g | Dow 282 | 2 Mil FEP/Teflon | 30 | ○ | — |
| GDE-9 | 1.00 g | Mom. PSA518 | 1 Mil PI/Kapton | 30 | ○ | ○ (backing) |
| GDE-10 | 1.00 g | Mom. PSA518 | 1 Mil PI/Kapton | 60 | ○ | — |
| GDE-11 | 1.00 g | Mom. PSA518 | 1 Mil PI/Kapton | 85 | ○ | — |
| GDE-12 | 1.00 g | Mom. PSA518 | 2 Mil FEP/Teflon | 30 | ○ | ○ (backing) |
| GDE-13 | 1.00 g | Mom. PSA518 | 2 Mil FEP/Teflon | 30 | ○ | ○ (adhesive) |
| GDE-14 | 1.00 g | Mom. PSA518 | 1 Mil PE | 30 | ○ | ○ (backing) |
| GDE-15 | 1.00 g | Mom. PSA518 | 1 Mil PET/Mylar | 30 | ○ | ● (backing) |
| GDE-24 | 1.00 g | Mom. PSA518 | 2 Mil PET/UVA | 30 | ○ | ○ (backing) |

Notes:
UVA: — Backing also comprises a UV Absorber.
○: No activation of chemochromic pigment
●: Chemochromic pigment was activated completely (Color was changed)
◐: Chemochromic pigment was activated partially (Color was changed, but not fully)
—: Not tested
(backing): UV was irradiated from backing side
(adhesive): UV was irradiated from adhesive side
2 Mil PET/UVA is Toray Lumirror U-65V Example 3.2 Effect of Release Liner GDE-9 was produced in a scaled up size of 600 mm width×100 yds and then wound up on one core to make a bundle roll.

When this bundle roll was stored in a warehouse for 7 days at ambient conditions, the color of the adhesive inside of the bundle roll layers had prematurely changed into black. This chemochromic activation occurred due to residual radicals from the crosslinking step and due to an insufficient supply of air (oxygen) because the second surface of the gas detection layer was adhered on the second surface of the backing.

In this situation, no ambient air (oxygen) can penetrate into the gas detection element, hence causing this premature chemochromic activation.

On the other hand, when GDE-9 was laminated with a release liner on the gas detection layer and the gas detection element was wound up into a bundle roll, premature color-change (chemochromic activation) inside of the bundle roll layers was not observed. The presence of the release liner caused a gap or space to be created between the backing and the release liner, allowing air (oxygen) to penetrate in. The release liner is 2 mil PET (2 mil clear Polyester "S Take off" from Loparex) coated with fluoro Si release agent. 2 mil PET seems to have sufficient air (oxygen) permeability to avoid premature chemochromic activation.

Example 3.3 Characterization of Experimental Results

Characterization of Sensitivity to Hydrogen.

To determine the timeframe for exposure, a selected embodiment of gas detection elements were measured to determine their color change response to the presence of hydrogen gas as a function of time. The color of the embodiments was measured with a color analyzer (PCM+, ColorTec Associates, Inc.) before exposure to hydrogen gas. The color was recorded. When required, the color analyzer was calibrated with a standard white panel included with the unit. After initial measuring the samples were placed in the test setup. Then the embodiments were each mounted to a flexible PTFE frame small enough to be placed in a 30 mL glass vial. The vial had a lid with an inlet port and an exhaust port so that it could be sealed and the inlet port connected in fluid communication to a source of gas and an exhaust port vent. Then, after the mounted sample was placed in the glass vial and sealed, 100% $H_2$ gas at 6 mL/min at room temperature was then flowed through the vial for 1 minute. After 1 minute, the gas flow was stopped, the vial vented, and the sample removed. After removal, the sample was then re-measured with the color analyzer (PCM+, ColorTec) to determine its color. The color change ($\Delta L^*$) was then calculated as the difference between the color after exposure and the color before exposure. The experiment was re-run with new samples of the same embodiment at times of 1.5 minutes, 2 minutes, 2.5 minutes, 5 minutes, and 20 minutes. A total of three samples were run for each time with the exception of the 5 minute sample and the 20 minute sample, where a single sample was run. The single control sample was not exposed. The sample exposed to five minutes of hydrogen had a color change that was greater than 5. Requiring a color change of equal or greater than 5 upon detection requires indicating performance of at least this order so that the color change is easy to recognize. This experiment also showed that the majority of color change occurred in the samples after 5 minutes of exposure to 100% $H_2$ gas at 6 mL/min at room temperature.

In addition, samples of embodiment GDE-9, an embodiment with a SilGrip*® PSA518 polymer matrix with a 5.5 wt % pigment to silicone PSA solids ratio, was tested to find when the samples turned the maximum color. The procedure is the same as above with the exception that the single samples were measured after exposure at varying lengths of time for varying flow rates and concentrations of $H_2$ gas as in Table 4. As shown in the table, at 100% $H_2$ gas at 6 mL/min an exposure of 5 minutes, Test A-3, would result in a color change comparable to the full color change as if the sample were left exposed for a longer period of time, or Test A-4.

TABLE 4

Examination of Time to Maximum Color Change as a Function of $H_2$ Gas Concentration and Flow Rate for GDE-9.

| Test # | Temp (° C.) | $H_2$ Gas Concentration | Flowrate (mL/min) | Exposure Time (min) | $L^*_{initial}$ | $L^*_{final}$ | $\Delta L^*$ |
|---|---|---|---|---|---|---|---|
| A-1 | 25 | 100% $H_2$ | 6 | 2 | 34.80 | 51.31 | 16.51 |
| A-2 | 25 | 100% $H_2$ | 6 | 2.5 | 34.80 | 51.26 | 16.46 |
| A-3 | 25 | 100% $H_2$ | 6 | 5 | 34.80 | 52.37 | 17.57 |
| A-4 | 25 | 100% $H_2$ | 6 | 20 | 34.80 | 50.97 | 16.17 |
| B-1 | 25 | 1% $H_2/N_2$ | 6 | 85 | 34.80 | 50.17 | 15.37 |
| B-2 | 25 | 1% $H_2/N_2$ | 9 | 30 | 34.80 | 50.47 | 15.67 |
| B-3 | 25 | 1% $H_2/N_2$ | 18 | 30 | 34.80 | 51.50 | 16.7 |
| B-4 | 25 | 1% $H_2/N_2$ | 17 | 60 | 34.80 | 51.61 | 16.81 |
| B-5 | 25 | 1% $H_2/N_2$ | 13 | 85 | 34.80 | 49.14 | 14.34 |
| B-6 (Ex.) | 25 | 1% $H_2/N_2$ | 65 | 3 | 34.80 | ~50.00 | ~15.20 |
| C-1 | 25 | 0.01% $H_2/N_2$ | 18 | 60 | 35.32 | 41.84 | 6.52 |
| C-2 | 25 | 0.01% $H_2/N_2$ | 18 | 75 | 35.32 | 46.36 | 11.04 |
| C-3 | 25 | 0.01% $H_2/N_2$ | 13 | 90 | 35.32 | 44.72 | 9.40 |
| C-4 | 25 | 0.01% $H_2/N_2$ | 9 | 120 | 35.32 | 41.14 | 5.82 |
| C-5 | 25 | 0.01% $H_2/N_2$ | 6 | 240 | 35.32 | ~35.32 | — |
| D-1 | 25 | 3% $H_2$/Air | 100 | 60 | 36.39 | 45.31 | 8.92 |
| D-2 | 25 | 2% $H_2$/Air | 100 | 120 | 36.39 | 41.76 | 5.37 |
| D-3 | 25 | 2% $H_2$/Air | 100 | 360 | 36.39 | 46.86 | 10.47 |
| D-4 | 25 | 1% $H_2$/Air | 100 | 1440 | 35.74 | 42.76 | 7.02 |
| D-5 | 25 | 1% $H_2$/Air | 100 | 1920 | 35.74 | 45.28 | 9.54 |
| E-1 | 25 | 3% $H_2$/Air | 25 | 120 | 36.39 | 41.91 | 5.52 |
| E-2 | 25 | 3% $H_2$/Air | 100 | 120 | 36.39 | 46.69 | 10.3 |

(Ex)—indicates data point extrapolated by examination of other data.

Example 3.4: Characterization of Experimental Results

Examination of Element Performance/Sensitivity to Hydrogen.

The gas detection elements were measured to determine their color change response to the presence of hydrogen gas. The color of the embodiments was measured with a color analyzer (PCM+, ColorTec Associates, Inc.). The color was recorded. When required the color analyzer was calibrated with a standard white panel included with the unit. After initial measuring the samples were placed in the test setup described in Example 3.2. The embodiments were mounted to a flexible PTFE frame small enough to be placed in the 30 mL glass vial. After the mounted sample was placed in the glass vial and sealed, 100% $H_2$ gas at 6 mL/min at room temperature was then flowed through the vial for 5 minutes. After 5 minutes, the gas flow was stopped, the vial vented, and the sample removed. After removal, the sample was then re-measured with the color analyzer (PCM+, ColorTec Associates, Inc.) to determine its color. The color change ($\Delta L^*$) was then calculated as the difference between the color after exposure and the color before exposure. In order to recognize color change easily, the value of the color change needs to be at least 5. The results for selected embodiments are shown in Table 5. As shown, all elements tested met the criteria when exposed to an oxygen-containing gas, or air, as part of the fabrication process in order to protect the pigment from premature activation.

TABLE 5

$H_2$ Performance Results for Selected Elements.

| Type | wt % Pigment to Silicone Solids | Thick. (µm) | Actual Thick. (µm) | $L^*_{initial}$ | $L^*_{final}$ | Avg. $L^*_{final}$ | $\Delta L^*$ | Meet Criteria ? |
|---|---|---|---|---|---|---|---|---|
| GDE-16 | 4.09 | 30 | 32 | 37.97 | 49.74 | 50.38 | 12.41 | Yes |
|  |  |  | 31 |  | 51.02 |  |  |  |
| GDE-17 | 4.5 | 20 | 18 | 36.76 | 41.54 | 42.27 | 5.51 | Yes |
|  |  |  | 18 |  | 42.99 |  |  |  |
| GDE-18 | 4.5 | 40 | 42 | 39.32 | 55.52 | 55.75 | 16.43 | Yes |
|  |  |  | 41 |  | 55.98 |  |  |  |
| GDE-19 | 5.5 | 15 | 17 | 36.61 | 47.21 | 47.52 | 10.91 | Yes |
|  |  |  | 17 |  | 47.82 |  |  |  |
| GDE-9 | 5.5 | 30 | 27 | 36.76 | 53.03 | 53.00 | 16.24 | Yes |
|  |  |  | 27 |  | 52.96 |  |  |  |
| GDE-9 | 5.5 | 30 | 26 | 38.49 | 52.07 | 52.74 | 14.25 | Yes |
|  |  |  | 27 |  | 53.40 |  |  |  |
| GDE-9 | 5.5 | 30 | 27 | 37.86 | 52.30 | 52.36 | 14.50 | Yes |
|  |  |  | 26 |  | 52.42 |  |  |  |
| GDE-20 | 5.5 | 45 | 42 | 41.14 | 57.67 | 58.07 | 16.93 | Yes |
|  |  |  | 41 |  | 58.46 |  |  |  |

TABLE 5-continued

H₂ Performance Results for Selected Elements.

| Type | wt % Pigment to Silicone Solids | Thick. (μm) | Actual Thick. (μm) | $L^*_{initial}$ | $L^*_{final}$ | Avg. $L^*_{final}$ | $\Delta L^*$ | Meet Criteria ? |
|---|---|---|---|---|---|---|---|---|
| GDE-21 | 6.5 | 20 | 20 21 | 36.83 | 51.34 51.55 | 51.45 | 14.62 | Yes |
| GDE-22 | 6.5 | 40 | 42 43 | 42.05 | 59.05 59.45 | 59.25 | 17.20 | Yes |
| GDE-23 | 6.91 | 30 | 31 30 | 40.30 | 56.83 57.17 | 57.00 | 16.70 | Yes |

Example 4.1 Manufacturing of Gas Detection Element

By the following method, a gas detection element (hereinafter referred to as "GDE-A") including chemochromic pigment particles was manufactured.

The gas detection element had a configuration including a backing material, a primer layer, and a gas detection layer including chemochromic pigment particles (also referred to as an "adhesive layer"), in the stated order.

As the backing material, polyimide (Kapton) (Dupont High Performance Films Circleville, Ohio, USA) having an area size of 30 cm×40 cm and a thickness of 1 mil was used.

The primer layer was formed by the following method.

A polysiloxane (SilGrip* SS4195A-D1, Momentive) including 15.06 g of a methylphenylsiloxane group was dissolved in 96.61 g of xylene at room temperature, and was then sufficiently stirred, to obtain a uniform solution. In the stirring state, 0.34 g of a cross-linking agent (SilForce* SS4191B, Momentive) was added to this solvent, and the solvent was further stirred for several minutes. Next, 0.567 g of an accelerator (SilForce* SS4259C, Momentive), and 0.567 g of a catalyst (SilForce* SS4192C, Momentive) were sequentially added, and the solvent was stirred for several minutes. Accordingly, a coating liquid for the primer layer (U-1) was obtained.

Next, in the obtained treatment liquid, 12.79 g of the above chemochromic composition was added, and was sufficiently stirred until a uniform liquid was obtained.

Accordingly, a coating mixture (C-1) was obtained.

The gas detection element was fabricated as follows.

First, on a backing material, a coating liquid (U-1) for the primer layer having a thickness of approximately 0.5 μm was coated.

Subsequently, this was dried at a temperature of 120° C. for 1 min, and a primer layer was formed.

Next, a bar coater (SA-210, Baker-Type-Applicator, Tester Sangyo Co., Ltd., Saitama-Ken, Japan) was used to coat the primer layer with the coating mixture (C-1).

Next, the backing material coated by the primer layer and the coating mixture, was dried between 30 seconds to 3 minutes at 25° C., to remove the solvent. Next, this backing material was retained in an oven for 3 minutes at 177° C. Accordingly, the gas detection element (GDE-A) was obtained.

The following table 6 schematically indicates the specifications of the configuration of the gas detection element (GDE-A).

TABLE 6

Configuration of Gas Detection Element

| | Gas Detection Layer | | | | | | |
|---|---|---|---|---|---|---|---|
| | Mass Quantities (g) | | | | PSA | Thickness | Backing |
| Element | CC-1 | MEK | BPO | Toluene | PSA Material | (μm) | Material |
| GDE-A | 2.39 | 10.4 | 1.0 | 28.0 | 75.0 Mom. PSA518 | 35 | 1 Mil PI/Kapton |

As the chemochromic pigment particles, the chemochromic pigment element CC-1 prepared in Example 1.1 above was used. 2.39 g of CC-1 was sufficiently dispersed in 10.4 g of methyl ethyl ketone (Aldrich), to fabricate a chemochromic dispersion liquid.

The coating mixture for the gas detection layer was prepared by the following method.

First, 1.0 g of benzoyl peroxide (97%, Luperox® A98, Aldrich) was added to 10 g of toluene (Aldrich). The obtained solvent was stirred for one minute, to completely dissolve the benzoyl peroxide.

Next, all of this solvent and 18 g of toluene (Aldrich) were added to 75 g of an adhesive precursor (SilGrip*® PSA518, Momentive), and this was stirred for three minutes. Accordingly, a treatment liquid was fabricated.

Comparative Example 4.2 Manufacturing of Gas Detection Element

By the following method, a gas detection element (hereinafter referred to as "GDE-B") including chemochromic pigment particles was manufactured.

The gas detection element had a configuration in which a gas detection layer including chemochromic pigment particles was set on a backing material.

As the backing material, a polyethylene film (U-LineS1113, nominal thickness 2 Mil) having a size of 30 cm×40 cm and a thickness of 45 μm was used.

The gas detection layer was formed as follows.

2.9 g of the chemochromic pigment element CC-1 was added into 10 g of a silicone sealant (Dow Corning® 734 Flowable Sealant), and this mixture was sufficiently stirred.

This mixture was applied on the backing material, and was dried for 24 hours at room temperature. Accordingly, a gas detection layer having a thickness of approximately 200 µm was formed on the backing material.

(Evaluation)

The two types of gas detection elements (GDE-A and GDE-B) described above were evaluated for the adhesion of the gas detection layers.

The adhesion of the gas detection layers was evaluated according to a 180° peel strength test using the following method.

Measurement samples were fabricated wherein the gas detection elements (GDE-A and GDE-B) were cut into a size of a width of 1 inch and a length of 18 inches. In the following paragraphs, a measurement sample obtained from the gas detection element GDE-A is referred to as "sample A". A measurement sample obtained from the gas detection element GDE-B is referred to as "sample B".

Next, in atmospheric air with a temperature of 23° C. and a relative humidity of 50% RH, on a stainless steel sheet (Type 304), the samples were placed such that the gas detection layer is facing downward. Next, on the sample, a rubber roller weighing 2 kg was moved back and forth once, to pressure bond the sample on the surface of the stainless steel sheet. After the pressure bonding, the following test was performed within one minute.

Next, a tensile testing machine (5565PA656, or 33R 4465P4758, Instron corp.) was used to perform the 180° peel strength test on each sample. The adhesion angle was 180°, and the tensile speed was 300 mm/minute.

Note that the above evaluation was performed in compliance with ASTM D 3330, Method D.

As a result, the adhesion of the sample A was 4.9 N/25 mm. On the other hand, the sample B came off immediately, and the adhesion could not be measured.

Note that as the target of pressure bonding, instead of a sole stainless steel sheet, a stainless steel having a paint (All Surface Enamel High Gloss 6509-00715 Safety Yellow, The Sherwin Williams Company) applied was used, and the same evaluation was made. As a result, the adhesion of the sample A was 5.5±1.0 N/25 mm. On the other hand, the sample B came off immediately, and the adhesion could not be measured.

Furthermore, the same evaluation was carried out by using a polyimide film as the target of pressure bonding. The target of pressure bonding was formed by placing a polyimide film having a thickness of 0.025 mm on the surface of the aforementioned stainless steel sheet, via an adhesive.

The sample A was placed on the surface of the polyimide film so that the gas detection layer faced the polyimide film, and a roller was moved back and forth once over the backing side of the sample A with a load of 2 kg. Accordingly, the sample A was adhered to the polyimide film, and a test specimen was formed.

As a result of measurement using this test specimen, the adhesion of the sample A was 4.4 N/25 mm. Note that in this experiment, it was confirmed that peeling occurred between the polyimide film and the sample A.

Next, a similar evaluation was carried out by using other gas sensing elements C and D.

The gas sensing element C was fabricated by the same method as that of the aforementioned GDE-A. However, the coating mixture for the gas detection layer was prepared by the following method.

20 g of SPUR+* PSA 3.0 (Momentive urethane silicone hybrid condensation crosslinking type solid content 40%) and 100 g of ethyl acetate were stirred and mixed to obtain a solution. 0.46 g of CC-1 was dispersed in 5 g of MEK and this was mixed with the above solution. Accordingly, a coating mixture for the gas detection layer was prepared.

The other steps are the same as those of the aforementioned GDE-A.

On the other hand, the gas detection element D was also manufactured by the same method as the aforementioned GDE-A. However, the coating mixture for the gas detection layer was prepared by the following method.

In 35 g of SilGrip* PSA 6574 (Momentive peroxide crosslinked silicone), 0.5 g of benzoyl peroxide dissolved in 13 g of toluene, was stirred and mixed, to obtain a solution. 1.1 g of CC-1 was dispersed in 5 g of MEK and this was mixed with the above solution. Accordingly, a coating mixture for the gas detection layer was prepared.

The other steps are the same as those of the aforementioned GDE-A.

Samples C and D were fabricated from the gas sensing elements C and D, respectively, and were evaluated, by the same method as described above. The target of pressure bonding was a stainless steel sheet.

As a result of the measurement, the adhesion of sample C was 1.4 N/25 mm. The adhesion of sample D was 5.3 N/25 mm.

Example 4.3 Evaluation of Gas Detection Element

By the following method, an evaluation test of color change properties of the gas detection element was performed.

(Measurement Sample)

First, by the example 4.1 described above, the tape type gas detection element (GDE-A) having a width of 5 cm was fabricated. Hereinafter, this gas detection element is referred to as a "measurement sample".

Next, a syringe having an inside diameter of 10 mm (capacity 24 ml) was prepared. Both ends of the syringe are open, and at substantially in the middle of the side surface of the syringe, one hole (through-hole) having a diameter of 2 mm is formed.

Next, the measurement sample was wound once around the side surface of this syringe, so as to block the through-hole of the syringe. At this time, a spacer was set between the gas detection layer and the syringe (at the opening of the through-hole). As the spacer, paper having a diameter of 12 mm was used.

Figure 18:
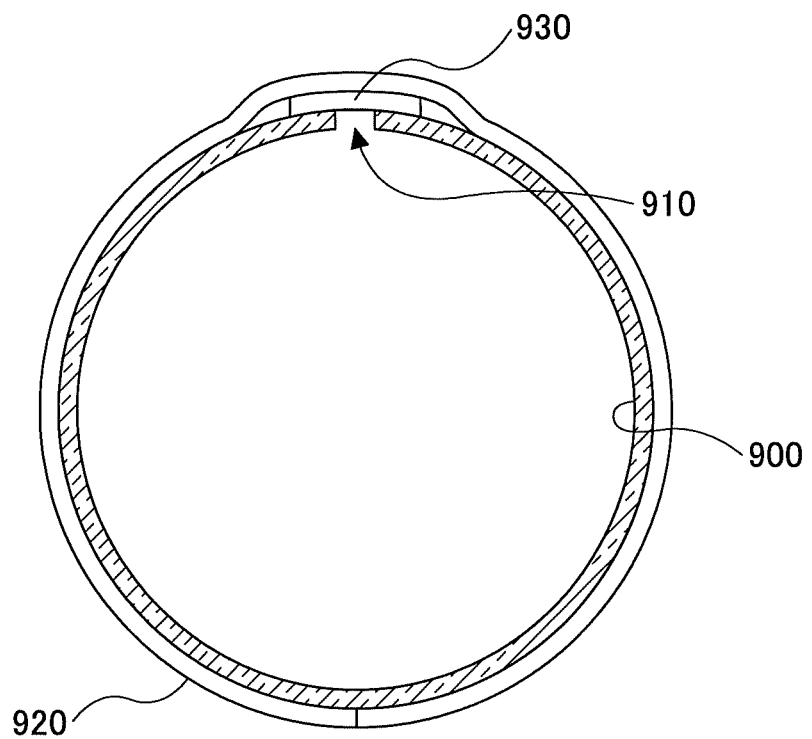
FIG. 18 is a schematic of an assembly used in example 4.3.

FIG. 18 is a schematic illustrating how the measurement sample is wound around the syringe. FIG. 18 illustrates a cross-section passing through the through-hole of the syringe.

As illustrated in FIG. 18, a measurement sample 920 is wound around the side surface of a syringe 900 including a through-hole 910. Furthermore, directly above the through-hole 910, a spacer 930 is set so as to block the through-hole 910. Therefore, the measurement sample 920 is set around the syringe 900 so as to cover this spacer 930.

Next, in the assembly illustrated in FIG. 18, hydrogen gas was passed through from one end to the other end of the syringe 900, at room temperature. The flow rate of the hydrogen gas was 6 ml/min., and the flow time was 5 minutes.

The hydrogen gas was caused to flow at approximately atmospheric pressure. These conditions were sufficient for the air in the syringe 900 to be replaced by hydrogen, and subsequently for the flow of hydrogen gas to be in a steady state.

After 5 minutes passed, the flow of the hydrogen gas was stopped, and the measurement sample 920 was retrieved.
(Evaluation)

By the above method, the color change (ΔL*) of the measurement sample was evaluated.

As the color meter, Color Meter (PCM+: manufactured by Color Tec) was used, to measure the measurement sample from the side of the backing material.

As a result of the measurement, the color change (ΔL*) was 18.

Furthermore, the area where the color change (ΔL*) has become greater than or equal to 5 (size of colored area) was measured from the side of the backing material of the measurement sample. As a result, the size of the colored area was 1.8 cm².

Example 4.4 Evaluation of Gas Detection Element

By the same method as example 4.3, an evaluation test of color change properties of the gas detection element was performed.

However, in the example 4.4, as the spacer that is set between the gas detection layer and the syringe (at the opening of the through-hole), a melamine foam having a thickness of 3 mm and a width of 10 mm was used. The spacer had a length that is equal to the outer circumference of the syringe, and the spacer was wound around the syringe such that both ends of the spacer substantially contact each other without overlapping each other.

After passing the hydrogen gas, the measurement sample was retrieved, and the same evaluation as example 4.3 was performed. As a result, the color change (ΔL*) was 18. Furthermore, the size of the colored area, where the color change (ΔL*) has become greater than or equal to 5, was 13.2 cm².

Example 4.5 Evaluation of Gas Detection Element

By the same method as example 4.3, an evaluation test of color change properties of the gas detection element was performed.

However, in the example 4.5, as the spacer that is set between the gas detection layer and the syringe (at the opening of the through-hole), an ethylene propylene diene rubber (EPDM) foam (EPT-Sealer #685 grey: manufactured by NITTO DENKO CORPORATION) having a thickness of 5 mm and a width of 10 mm was used. The spacer had a length that is equal to the outer circumference of the syringe, and the spacer was wound around the syringe such that both ends of the spacer substantially contact each other without overlapping each other.

After passing the hydrogen gas, the measurement sample was retrieved, and the same evaluation as example 4.3 was performed. As a result, the color change (ΔL*) was 13. Furthermore, the size of the colored area, where the color change (ΔL*) has become greater than or equal to 5, was 10.0 cm².

Example 4.6 Evaluation of Gas Detection Element

By the same method as example 4.3, an evaluation test of color change properties of the gas detection element was performed.

However, in the example 4.6, as the spacer, a pattern of acrylic adhesive layers was used.

More specifically, a pattern of adhesive layers arranged in parallel lines adjacent to each other was set along the longitudinal direction, on the surface of the gas detection layer of the measurement sample. The length between adjacent lines was approximately 3 mm and the width of each line of the adhesive layers was 75 μm. Furthermore, the thickness of each adhesive layer was 75 μm.

After passing the hydrogen gas, the measurement sample was retrieved, and the same evaluation as example 4.3 was performed. As a result, the color change (ΔL*) was 18. Furthermore, the size of the colored area, where the color change (ΔL*) has become greater than or equal to 5, was 3.0 cm².

The following table 7 shows the evaluation results obtained in examples 4.3 to 4.6.

TABLE 7

| Example | Spacer Type | Color-changed area (cm²) | ΔL* |
|---|---|---|---|
| 4.3 | Paper | 1.8 | 18 |
| 4.4 | Melamine Foam | 13.2 | 18 |
| 4.5 | EPDM Foam | 10.0 | 13 |
| 4.6 | a pattern of acrylic adhesive layers | 3.0 | 18 |

Example 5

Example 5.1

Changes in color before and after the color reaction were evaluated using the gas sensing element according to an embodiment of the present invention.

As the gas sensing element, the above-mentioned GDE-A was cut into a size of 40 mm in length×40 mm in width (hereinafter referred to as "sample 5.1"). Sample 5.1 was exposed to a hydrogen environment to completely change the color of the gas detection layer.

The chroma of the color was measured by using sample 5.1 before use and sample 5.1 after change in color. For the measurement, a spectral color difference meter (SE 6000; Nippon Densyoku Industries Co., Ltd.) was used, and a C light source (2° field of view) was used as a light source. The measurement size of this device was a diameter of 28 mm, and the measurement was performed from the side of the substrate near the center of sample 5.1. Note that the measurement was carried out indoors.

From the measurement results, the chroma of the color difference ΔC* before and after the color reaction was obtained.

Here, as described above, the chroma of the color difference ΔC* can be calculated from formula (1), where $C^*_{initial}$ is the chroma of the color of sample 5.1 before use, and $C^*_{final}$ is the chroma of the color of sample 5.1 after the color has changed:

$$\Delta C^* = |C^*_{final} - C^*_{initial}| \qquad \text{formula (1)}$$

The result of measurement was chroma of the color difference ΔC*=|32.43−55.11|=22.68.

Example 5.2

By the same method as in example 5.1, the chroma of the color difference ΔC* before and after the color reaction in another gas sensing element according to an embodiment of the present invention, was evaluated.

However, in example 5.2, sample 5.2 was used instead of sample 5.1. Sample 5.2 has the same configuration as that of sample 5.1, except that sample 5.2 was different from sample 5.1 in that the substrate was transparent polyethylene terephthalate (PET) (Lumirror; Toray Industries, Inc.) having a thickness of 75 µm.

The result of measurement was chroma of the color difference ΔC*=|14.77−1.3|=13.47.

Example 5.3

By the same method as in example 5.1, the chroma of the color difference ΔC* of yet another gas sensing element according to an embodiment of the present invention, was examined.

Figure 19:
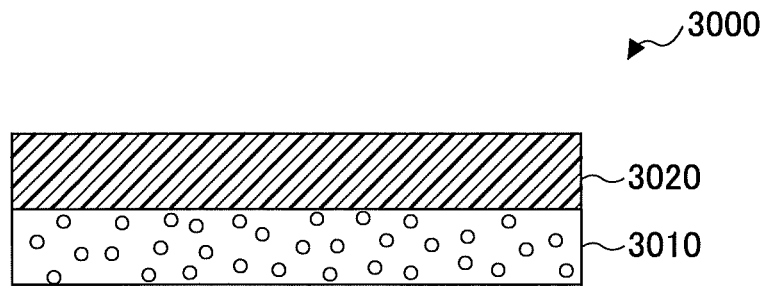
FIG. 19 is a cross-sectional diagram schematically depicting a configuration of the gas sensing element according to example 5.3.

Note that as a sample of the gas sensing element, the configuration illustrated in FIG. 19 was applied.

As illustrated in FIG. 19, a sample 3000 includes a gas detection layer 3010 and a colored substrate 3020. Among these, the configuration of the gas detection layer 3010 is the same as that of the above-described sample 5.1.

On the other hand, the colored substrate 3020 is formed of a red substrate having a thickness of 17 µm.

However, since it was difficult to actually fabricate the sample 3000 having the configuration illustrated in FIG. 19, in this example, a simulated sample of the sample 3000 was prepared and the chroma of the color difference ΔC* of the simulated sample was evaluated.

Figure 20:
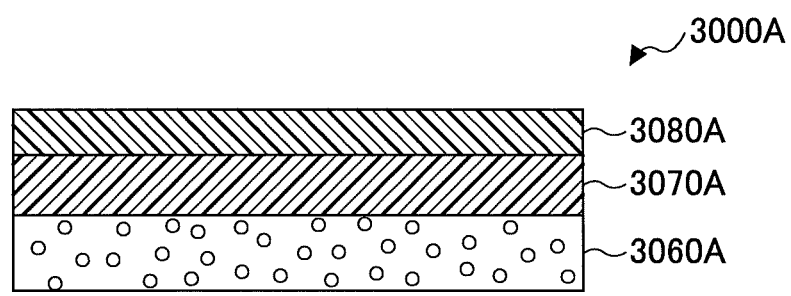
FIG. 20 is a cross-sectional diagram schematically depicting a configuration of a simulated sample used in example 5.3.

FIG. 20 schematically depicts a cross-section of the actually fabricated simulated sample 3000A.

As illustrated in FIG. 20, the simulated sample 3000 A is formed by laminating a gas detection layer 3060A, a first substrate 3070A formed of PET, and a second substrate 3080A formed of a color film, in the stated order.

Among these, the configuration from the gas detection layer 3060A to the first substrate 3070A is the same as that of the above-described sample 5.2. On the other hand, the second substrate 3080A was a red cellophane (KOMODA; Komoda Paper Co., Ltd.) having a thickness of 17 µm.

Here, as is clear from the comparison between FIG. 19 and FIG. 20, the simulated sample 3000A is different from the sample 3000 in that the first substrate 3070A made of PET is added. Therefore, in order to appropriately evaluate the chroma of the color difference ΔC* in the sample 3000, it is necessary to consider the influence of the first substrate 3070A included in the simulated sample 3000A on the chroma of the color difference ΔC*, that is, on the $C^*_{initial}$ and the $C^*_{final}$.

Therefore, here, another gas sensing element (hereinafter referred to as a "correction sample") was fabricated and the chroma of the color difference ΔC* of the correction sample was evaluated.

Figure 21:
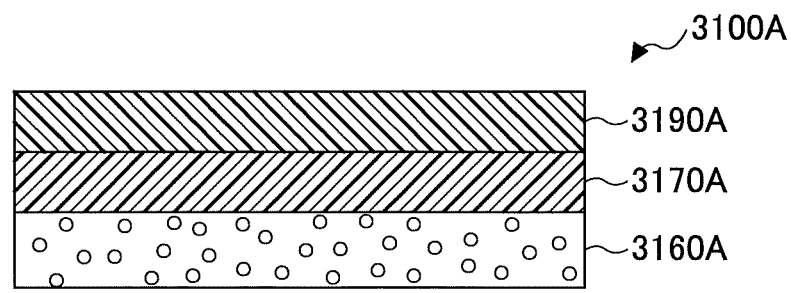
FIG. 21 is a cross-sectional diagram schematically depicting a configuration of a correction sample used in example 5.3.

FIG. 21 schematically illustrates the configuration of the correction sample.

As illustrated in FIG. 21, a correction sample 3100A is formed by laminating a gas detection layer 3160A, a first substrate 3170A made of PET, and a second substrate 3190A made of polyimide (1 mil, 100 PST Kapton, Dupont High Performance Films), in the stated order.

Here, the configuration from the gas detection layer 3160A to the first substrate 3170A is the same as that of the above-described sample 5.2. Furthermore, the second substrate 3190A is the same as the substrate in sample 5.1.

The correction sample 3100A illustrated in FIG. 21 is different from sample 5.1 only in that the first substrate 3170A made of PET is present. Therefore, by comparing the difference between $C^*_{initial}$ and $C^*_{final}$ in both configurations, it is possible to ascertain the influence of the first substrate 3170A made of PET on the chroma of the color difference ΔC*, and furthermore, to ascertain the influence of the first substrate 3070A made of PET in FIG. 20.

The results of measurement using the correction sample 3100A illustrated in FIG. 21, were $C^*_{initial}$=45.71 and $C^*_{final}$=27.53. On the other hand, in Sample 5.1, the results were $C^*_{initial}$=55.11 and $C^*_{final}$=32.43 as described above. Therefore, in the correction sample 3100A illustrated in FIG. 21, compared with sample 5.1, the value of $C^*_{initial}$ deviates by 45.71−55.11=−9.4, and the value of $C^*_{final}$ deviates by 27.53−32.43=−4.9.

Therefore, in the case of the configuration illustrated in FIG. 20, that is, in the case of the configuration in which the first substrate 3070A made of PET is further added directly under the second substrate 3080A made of a color film, it is inferred that the above deviation amount will occur compared to the configuration of FIG. 19.

Based on the above consideration, the chroma of the color difference ΔC* in sample 3000 (hereinafter referred to as "sample 5.3") illustrated in FIG. 19 can be obtained from the above formula (1), upon adding 9.4 to $C^*_{initial}$ obtained in sample 3000A in FIG. 20, and adding 4.9 to $C^*_{final}$ obtained in sample 3000A in FIG. 20.

Results of the measurement of sample 3000A were $C^*_{initial}$=39.88 and $C^*_{final}$=26.43. Therefore, the chroma of the color difference ΔC* in sample 5.3 is estimated as follows.

$$\Delta C^* = |(39.88+9.4)-(26.43+4.9)| = 17.95$$

Example 5.4

By the same method as in example 5.3, the chroma of the color difference ΔC* in yet another gas sensing element according to an embodiment of the present invention, was examined.

Here, however, a blue cellophane (KOMODA; Komoda Paper Co., Ltd.) having a thickness of 17 µm was applied as a colored substrate 3020 included in the gas sensing element (hereinafter referred to as "sample 5.4").

Furthermore, the chroma of the color difference ΔC* was calculated by the same procedure as in the case of the above example 5.3. That is, $C^*_{initial}$ and $C^*_{final}$ were measured using a simulated sample in which a first substrate made of PET was placed directly under the blue colored substrate, and from the obtained results, the chroma of the color difference ΔC* of sample 5.4 was calculated, in consideration of the influence of the above-mentioned first substrate made of PET.

As a result, the chroma of the color difference ΔC*=|(17.33+9.4)−(18.35+4.9)|=3.48 of sample 5.4 was calculated.

Example 5.5

By the same method as in example 5.3, the chroma of the color difference ΔC* of yet another gas sensing element according to an embodiment of the present invention, was examined.

Here, however, a yellow cellophane (KOMODA; Komoda Paper Co., Ltd.) having a thickness of 16 µm was applied as a colored substrate 3020 included in the gas sensing element (hereinafter referred to as "sample 5.5").

Furthermore, the chroma of the color difference ΔC* was calculated by the same procedure as in the case of the above example 5.3. That is, $C^*_{initial}$ and $C^*_{final}$ were measured using a simulated sample in which a first substrate made of PET was placed directly under the yellow colored substrate, and from the obtained results, the chroma of the color difference $\Delta C^*$ of sample 5.5 was calculated, in consideration of the influence of the above-mentioned first substrate made of PET.

As a result, the chroma of the color difference $\Delta C^* = |(54.85+9.4)-(34.13+4.9)| = 25.22$ of sample 5.5 was calculated.

Example 5.6

By the same method as in example 5.3, the chroma of the color difference $\Delta C^*$ of yet another gas sensing element according to an embodiment of the present invention, was examined.

Here, however, a green cellophane (KOMODA; Komoda Paper Co., Ltd.) having a thickness of 18 μm was applied as a colored substrate 3020 included in the gas sensing element (hereinafter referred to as "sample 5.6").

Furthermore, the chroma of the color difference $\Delta C^*$ was calculated by the same procedure as in the case of the above example 5.3. That is, $C^*_{initial}$ and $C^*_{final}$ were measured using a simulated sample in which a first substrate made of PET was placed directly under the green colored substrate, and from the obtained results, the chroma of the color difference $\Delta C^*$ of sample 5.6 was calculated, in consideration of the influence of the above-mentioned first substrate made of PET.

As a result, the chroma of the color difference $\Delta C^* = |(29.31+9.4)-(20.12+4.9)| = 13.69$ of sample 5.6 was calculated.

In the following Table 8, the chroma of the color differences $\Delta C^*$ obtained in the configurations of the respective gas sensing elements are indicated.

TABLE 8

| Sample | $L^*_{initial}$ | $L^*_{final}$ | $\Delta L^*$ | $C^*_{initial}$ | $C^*_{final}$ | $\Delta C^*$ |
|---|---|---|---|---|---|---|
| 5.1 | 36.11 | 22.75 | 13.36 | 55.11 | 32.43 | 22.68 |
| 5.2 | 43.63 | 30.16 | 13.47 | 14.77 | 1.30 | 13.47 |
| 5.3 | 20.97 | 12.12 | 8.85 | 49.28 | 31.33 | 17.95 |
| 5.4 | 15.63 | 10.11 | 5.52 | 26.73 | 23.25 | 3.48 |
| 5.5 | 36.32 | 23.70 | 12.62 | 64.25 | 39.03 | 25.22 |
| 5.6 | 21.84 | 13.76 | 8.08 | 38.71 | 25.02 | 13.69 |

Note that in Table 8, the values of $C^*_{initial}$ and $C^*_{final}$ in samples 5.3 to 5.6 are indicated by taking into consideration the aforementioned deviation. Furthermore, Table 8 also indicates the lightness difference $\Delta L^*$ for reference.

From these results, it was found that in samples 5.1 to 5.6, the chroma of the color difference $\Delta C^*$ before and after the color reaction was 3 or more (50 or less), indicating good color changes.

While various disclosed embodiments have been described above, it should be understood that they have been presented by way of example only, and not limitation. Numerous changes to the subject matter disclosed herein can be made in accordance with this disclosure without departing from the spirit or scope of this disclosure. In addition, while a particular feature may have been disclosed with respect to only one of several implementations, such feature may be combined with one or more other features of the other implementations as may be desired and advantageous for any given or particular application. Thus, the breadth and scope of the subject matter provided in this disclosure should not be limited by any of the above explicitly described embodiments. Rather, the scope should be defined in accordance with the following claims and their equivalents.

The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which embodiments of the invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. Notwithstanding that the numerical ranges and parameters are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

It should be understood that numerous specific details, relationships, and methods are set forth to provide a full understanding of the disclosed embodiments. One having ordinary skill in the relevant art, however, will readily recognize that the subject matter disclosed herein can be practiced without one or more of the specific details or with other methods. In other instances, well-known structures or operations are not shown in detail to avoid obscuring structures or operations that are not well-known. Groupings of alternative elements or embodiments disclosed herein are not to be construed as limitations. Each group member may be referred to and claimed individually or in any combination with other members of the group or other elements found herein. Furthermore, not all illustrated acts or events are required to implement a methodology disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

The invention claimed is:

1. An adhesive tape comprising:
   a gas detection layer including a pigment, the gas detection layer including a first surface; and
   a backing material disposed on the first surface of the gas detection layer, wherein
   when reducing gas causes the adhesive tape to change in color, a color change $\Delta L^*$ of the adhesive tape is greater than or equal to 5,
   the gas detection layer includes a pressure sensitive adhesive having an adhesive force such that, upon the gas detection layer being pressed against a target other than the adhesive tape itself, the adhesive tape is adhered to the target by the adhesive force of the pressure sensitive adhesive, and
   a gas permeability of the backing material is lower than a gas permeability of the gas detection layer.

2. The adhesive tape of claim 1, farther comprising:
   a diffusion part where the reducing gas is diffused, on a second surface of the gas detection layer opposite to the first surface of the gas detection layer.

3. The adhesive tape of claim 2, further comprising:
   a spacer for forming the diffusion part, the spacer being set on the second surface of the gas detection layer.

4. The adhesive tape of claim 3, wherein the spacer has a thickness of 5 μm to 10 mm.

5. The adhesive tape of claim 3, wherein the spacer is formed of paper, a non-woven, an adhesive layer, a foam, or a porous film, or a fibrous film.

6. The adhesive tape of claim 1, wherein the reducing gas includes at least one of hydrogen, hydrogen sulfide, carbon monoxide, methane, formaldehyde, acetylene, sulfur dioxide, and nitrous oxide.

7. The adhesive tape of claim 1, wherein the pigment includes a chemochromic composition.

8. The adhesive tape of claim 1, wherein the pigment irreversibly changes in color, by contacting reducing gas.

9. The adhesive tape of claim 1, the gas detection layer further comprising carrier particles having a surface, the pigment including a palladium oxide, palladium hydroxide, or palladium salts on the surfaces of carrier particles.

10. The adhesive tape of claim 9, wherein a noble metal other than palladium is supported or loaded, on the surfaces of the carrier particles.

11. The adhesive tape of claim 9, wherein the carrier particles include titanium oxide.

12. The adhesive tape of claim 1, wherein the pressure sensitive adhesive includes an acrylic pressure sensitive adhesive, a silicone-based pressure sensitive adhesive, an urethane-based pressure sensitive adhesive, or a rubber-based pressure sensitive adhesive.

13. The adhesive tape of claim 12, wherein the silicone-based pressure sensitive adhesive includes a methylphenylsiloxy group or a dimethylsiloxy group.

14. The adhesive tape of claim 1, wherein the backing material includes polyimide; polyethylene; fluoro carbon polymer such as fluorinated ethylene propylene copolymer (FEP), ethylene tetrafluoroethylene copolymer (ETFE), poly tetra fluoro ethylene (PTFE), or tetra fluoro ethylene hexa fluoro propylene copolymer (PFA); or polyethylene terephthalate (PET) which contains IN absorber or hindered amine light stabilizers (HALS).

15. The adhesive tape of claim 1, wherein the adhesive tape is rolled up into a bundle roll-shape.

16. The adhesive tape of claim 1, wherein the gas detection layer has a release liner on a finished product or on a product that is in process of production.

17. The adhesive tape of claim 1, wherein the gas detection layer has a thickness of 10 μm to 100 μm.

18. The adhesive tape of claim 1, wherein the gas detection layer has an adhesion of greater than or equal to 0.2 N/25 mm.

19. The adhesive tape of claim 1, wherein
   a chroma of the color difference $\Delta C^*$ of the adhesive tape before and after a color reaction, is greater than or equal to 3:
   the chroma of the color difference $\Delta C^*$ is obtained by
   $$\Delta C^* = |C^*_{final} - C^*_{initial}|,$$
   where $C^*_{initial}$ represents a chroma of the color of the adhesive tape before use, and $C^*_{final}$ represents the chroma of the color of the adhesive tape after the color reaction.

* * * * *